(12) United States Patent
Wang et al.

(10) Patent No.: US 8,916,583 B2
(45) Date of Patent: Dec. 23, 2014

(54) THERAPEUTIC COMPOSITIONS FOR INTRANASAL ADMINISTRATION OF ZOLPIDEM

(71) Applicant: Renascence Therapeutics Limited, Hong Kong (CN)

(72) Inventors: Yanfeng Wang, Hong Kong (CN); Benjamin T. K. Lee, Hong Kong (CN); Tony C. Y. Ho, Hong Kong (CN); Melvin K. M. Toh, Hong Kong (CN)

(73) Assignee: Renascence Therapeutics Limited, Hong Kong (CN)

( * ) Notice: Subject to any disclaimer, the term of this patent is extended or adjusted under 35 U.S.C. 154(b) by 0 days.

(21) Appl. No.: 13/747,367

(22) Filed: Jan. 22, 2013

(65) Prior Publication Data

US 2013/0190349 A1    Jul. 25, 2013

Related U.S. Application Data

(60) Provisional application No. 61/588,672, filed on Jan. 20, 2012.

(51) Int. Cl.
| | | |
|---|---|---|
| *A61K 31/437* | (2006.01) | |
| *C07D 471/02* | (2006.01) | |
| *A61K 47/40* | (2006.01) | |
| *A61K 47/36* | (2006.01) | |
| *A61K 47/38* | (2006.01) | |
| *A61K 9/00* | (2006.01) | |
| *A61K 47/10* | (2006.01) | |
| *A61M 11/00* | (2006.01) | |

(52) U.S. Cl.
CPC ............... *A61K 47/40* (2013.01); *A61K 47/36* (2013.01); *A61K 47/38* (2013.01); *A61K 9/0043* (2013.01); *A61K 31/437* (2013.01); *A61K 47/10* (2013.01); *A61M 11/00* (2013.01)
USPC ............ 514/300; 546/112; 546/121; 514/299

(58) Field of Classification Search
CPC ........................... A61K 31/437; C07D 471/02
USPC ........................... 546/112, 121; 514/299, 300
See application file for complete search history.

(56) References Cited

U.S. PATENT DOCUMENTS

| | | | |
|---|---|---|---|
| 6,294,192 B1 * | 9/2001 | Patel et al. ............ 424/451 |
| 6,383,471 B1 * | 5/2002 | Chen et al. ............ 424/45 |
| 8,449,909 B2 * | 5/2013 | Hirsh et al. ........... 424/458 |
| 2004/0241100 A1 | 12/2004 | Kramer et al. | |
| 2006/0216240 A1 | 9/2006 | Dugger, III et al. | |
| 2007/0140981 A1 | 6/2007 | Castile et al. | |

FOREIGN PATENT DOCUMENTS

| | | |
|---|---|---|
| CN | 1660086 A | 8/2005 |
| WO | WO 2005/060945 A2 | 7/2005 |
| WO | WO 2008/141264 A1 | 11/2008 |

OTHER PUBLICATIONS

Trapani et al (2003): STN International HCAPLUS database, Columbus (OH), accession No. 2003: 915918.*
Clauss R, Nel W.; "Drug induced arousal from the permanent vegetative state."; *NeuroRehabilitation* 21; (2006); pp. 23-28.
Daniele Antonio, et al; "Zolpidem in Parkinson's disease" *Lancet* vol. 349; (1997); pp. 1222-1223.
Davis, Stanley S; Illum, Lisbeth; "Absorption enhancers for nasal drug delivery"; *Clin Pharmacokinet* 42(13): (2003); pp. 1107-1128.
Hindmarch et al.; "Residual effects of zaleplon and zolpidem following middle of the night administration five hours to one hour before awakening."; *Hum Psychopharcol* 16; (2001); pp. 159-167.
Martindale The Complete Drug Reference, 36th Edition, Pharmaceutical Press, (2009) Grayslake, USA; 5 pages.
Salva P, Costa J.; "Clinical pharmacokinetics and pharmacodynamics of zolpidem: therapeutic implications."; *Clin Pharmacokinet*, 29(3); (1995); pp. 142-153.
Xie Wei-rong, et al; "Advances in Research on in Situ Gel for Nasal Drug Delivery System"; Journal of Liaoning University of TCM, vol. 13, No. 7; Jul. 2011; pp. 61-64.
International Search Report and Written Opinion under Patent Cooperation Treat (PCT) for PCT/CN2013/070799; Dated Apr. 25, 2013; 11 pages.

* cited by examiner

*Primary Examiner* — Golam M M Shameem
(74) *Attorney, Agent, or Firm* — Duane Morris LLP; Siegfried J.W. Ruppert

(57) ABSTRACT

The invention provides sprayable aqueous compositions containing zolpidem or single stereoisomer, mixtures of stereoisomers, pharmaceutically acceptable salts or prodrugs thereof, a solubilizing agent, a water soluble polymer with bioadhesive property. When administered intranasally using a spray device, zolpidem is rapidly absorbed with prolonged intranasal residence time and improved bioavailability. The compositions can be applied for the treatment of insomnia-related disorders such as difficulties with sleep initiation or middle of the night awakenings.

20 Claims, 4 Drawing Sheets

THERAPEUTIC COMPOSITIONS FOR INTRANASAL ADMINISTRATION OF ZOLPIDEM

CROSS REFERENCE TO RELATED APPLICATIONS

This application claims benefit of provisional patent application Ser. No. 61/588,672, filed Jan. 20, 2012, the disclosure of which is incorporated in its entirety by reference for all purposes.

FIELD OF THE INVENTION

This invention relates to pharmaceutical compositions, particularly aqueous pharmaceutical compositions comprising zolpidem as the active ingredient for intranasal administration in short-term treatment of insomnia characterized by difficulties with sleep initiation or middle of the night awakenings.

BACKGROUND OF THE INVENTION

Zolpidem or N,N,6-trimethyl-2-(4-methylphenyl)-imidazo[1,2-a]pyridine-3-acetamide, with the formula as below (Formula I):

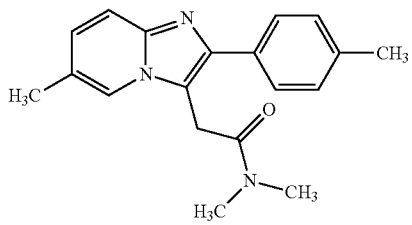

Formula I is an imidazopyridine with strong sedative actions, but only with mild anxiolytic, muscle relaxant, or anticonvulsant properties, Zolpidem acts by binding to the benzodiazepine receptor component of the GABA receptor complex, and has selective affinity for the subtype of benzodiazepine receptors prevalent in the cerebellum (BZ1- or ω1-receptors) as opposed to those more commonly found in the spinal cord (BZ2- or ω2-receptors) or in the peripheral tissues (BZ3- or ω3-receptors). Zolpidem has a rapid onset and short duration of hypnotic action and at usual doses (about 5-10 mg) decreases time to sleep onset and increases duration of sleep with little apparent effect on sleep stages (Page 1037, Martindale The Complete Drug Reference, 36th Edition, Pharmaceutical Press, Grayslake, USA, 2009). Meanwhile, zolpidem has also been reported in the treatment of Parkinson disease (Daniele A, et al. Zolpidem in Parkinson's disease. *Lancet* 1997; 349:1222-3), and the permanent vegetative state (Clauss R, Nel W. Drug induced arousal from the permanent vegetative state. *NeuroRehabilitation* 2006; 21: 23-8).

Zolpidem is rapidly absorbed from the gastrointestinal tract after oral doses, peak plasma concentrations being reached within 3 hours. Zolpidem undergoes first-pass metabolism and an absolute bioavailability of about 70% has been reported. Zolpidem has an elimination half-life of about 2.5 hours and is about 92% bound to plasma proteins. It is metabolized primarily by the cytochrome P450 isoenzyme CYP3A4 and the inactive metabolites of zolpidem are excreted in the urine and feces. Zolpidem is distributed into breast milk (Salvà P, Costa J. Clinical pharmacokinetics and pharmacodynamics of zolpidem: therapeutic implications. *Clin Pharmacokinet* 1995; 29: 142-53).

Generally, zolpidem is administered as oral tablets containing the hemitartrate salt of zolpidem, with the trade name of AMBIEM®. For short-term management of insomnia, a usual oral dose of 10 mg (5 mg for elderly) is taken about 1 hr before the bedtime. A modified-release formulation of zolpidem tartrate is also available. Zolpidem oral dosage forms are not recommended to be used as needed, especially for treating middle-of-the night awakenings, due to the next-day hangover effects (daytime drowsiness and sleepiness) when administered 1-5 hr before waking (Hindmarch et al. Residual effects of zaleplon and zolpidem following middle of the night administration five hours to one hour before awakening. *Hum Psychopharcol* 2001; 16(2):159-167).

People spend approximately ⅓ of their lives sleeping, and millions of people suffer from insomnia. The average adult, for example, should have 8 hours of sleep and usually gets about 6.9 hours of sleep. In 2005, the National Sleep Foundation survey showed about 75% of all adult Americans reported one or more symptoms of insomnia, and about 33% experienced insomnia almost every night. Caffeine consumption is suggested as a significant contributor to the problem.

The problem of insomnia is addressed by several mechanisms in the current market. The mechanisms are generally directed to affecting the level of naturally-occurring neurotransmitters in a subject or stimulating/inhibiting the subject's response to certain neurotransmitters. Benzodiazepine, for example, is considered a first line treatment. Benzodiazepine (BDZ) works on the GABA receptor and improves sleep quality, but it can cause severe side-effects. Non-BDZ drugs promote sleepiness and cause less side-effects, but they can cause amnesia. Both BDZ and non-BDZ drugs carry a dependency risk. Examples include Eszopiclone (LUNESTA®), flurazepam (DALMANE®), and zolpidem (AMBIEN®). Antidepressants are also used, including amitriptyline (ELAVIL®), mirtazapine (REMERON®), nefazodone (SERZONE®), doxepin (ZONALON®), and trazodone (DESYREL®). Problems with the antidepressants include, but are not limited to, risk of use in the elderly, lack of understanding mode of action, sedation, dizziness, weight gain, and increased risk with cardiovascular disease and high blood pressure. Some over-the-counter medications have also been administered to treat insomnia, such as diphenhydramine. Problems with diphenhydramine include carry-over sedation ("hangover") and tolerance effect. Other over-the-counter drugs that find such use include, but are not limited to, doxylamine, valerian root, and melatonin, where use is limited for at least the reasons of questionable effect and consistency. Other treatments include, for example, non-pharmacological methods of relaxation therapies, behavioral training, sleep hygiene, and stimulus control. Stimulus control (intake control) has been found to be the most effective behavioral intervention.

Several disorders have been shown to have insomnia as a co-morbid condition and/or relatively specific alterations in cerebral metabolism that may benefit from treatment with a frontal hypothermia device. These co-morbid conditions make medication treatment even more difficult, because these patients are often already on multiple other medications, some of which have sleep effects themselves. Co-morbid insomnia itself has been little studied with any form of treatment. Depression is associated with severe sleep disturbances including difficulty falling asleep, difficulty staying asleep, early morning awakening, or nonrestorative sleep. Functional neuroimaging studies have shown alterations in the normal reduction in prefrontal cortex metabolism from waking to NREM sleep. The lifetime prevalence of depression in the United States is 17.1% or currently 52 million individuals suggesting that this is a significant problem. The neurobiology of sleep problems in patients with chronic pain share significant overlaps with those of insomnia suggesting another medical disorder that may benefit from the treatment of insomnia. The most common causes of pain that disrupt sleep include back pain (cost to society estimated to exceed $100 billion each year), headaches (50% of whom sleep disturbances trigger headaches and 71% of migraine sufferers have migraines that awaken them from sleep), fibromyalgia, and arthritis (osteoarthritis, rheumatoid arthritis and autoimmune diseases such as lupus). Chronic pain prevalence estimates in the United States are 10.1% for back pain, 7.1% for pain in the legs/feet, 4.1% for pain in the arms/hands, and 3.5% for headache. Chronic regional and widespread pain, are reported by 11.0% and 3.6% of respondents, respectively. Based on US Census data, this would translate into an additional market of over 50 million individuals. 70-91% of patients with post-traumatic stress disorder (PTSD) have difficulty falling or staying asleep. Medical treatments for the sleep problems in PTSD have revolved around medication management, which have associated adverse events. Studies conducted as part of the National Comorbidity Survey (NCS) have reported the prevalence of lifetime PTSD in the United States as 7.8 percent or currently a market of over 23 million individuals.

Accordingly, and for at least the above reasons, one of skill will appreciate a method of treating insomnia and insomnia-related disorders that carry less risk of side-effects and are more predictable in efficacy.

Zolpidem pharmaceutical compositions described in the prior art (e.g., US2006/0216240, WO2008/141264, US2004/0241100, and US2007/0140981) have significant disadvantages, including decreased absorption by food, slow achievement of therapeutic blood levels, difficulties to prepare, store and applying them intranasally. Some even may induce moderate to server irritation to nasal mucosa depending on the concentration. In view of the issues existed in the prior art, there is a clear need for zolpidem compositions, which provide a substantially faster onset of action for zolpidem than existing zolpidem formulations and making it suitable for the management of insomnia characterized by difficulties with sleep initiation or managing middle-of-the-night awakenings without inducing severe side effects, for example, local irritation or next-day residual effects. There is also a need for zolpidem compositions that are easy to prepare, suitable for long-term storage and have superior intranasal applicability. The present invention provides such zolpidem compositions.

BRIEF SUMMARY OF THE INVENTION

The present invention provides zolpidem compositions; in particular zolpidem intranasal spray compositions. In some embodiments of the invention the intranasal spray composition comprises a biologically active pharmaceutical ingredient, e.g., zolpidem or single stereoisomer, mixtures of stereoisomers, pharmaceutically acceptable salts or prodrugs thereof; which can be rapidly and thoroughly absorbed from nasal mucosa after the spray is administrated, resulting in a substantially faster onset (i.e., less than 15 min) of sedative effects. In some embodiments, the composition delivers about 0.5 mg to about 20.0 mg zolpidem or single stereoisomer, mixtures of stereoisomers, pharmaceutically acceptable salts or prodrugs thereof after intranasal administration of a spray volume ranging from about 10 µL to about 200 µL in each nostril.

In some embodiments of the present invention, zolpidem or single stereoisomer, mixtures of stereoisomers, pharmaceutically acceptable salts or prodrugs thereof is dissolved in an aqueous medium containing a polymeric bioadhesive material. In some embodiments the polymeric bioadhesive material is used to prolong drug residence time and improve the rate and extend of drug absorption. In some embodiments of the present invention, zolpidem tartrate is mixed with a polymeric bioadhesive material selected from the group consisting of carboxymethylcellulose sodium, hyaluronic acid, hydroxylethylcellulose, hydroxypropylcellulose, hydroxymethylpropylcelloluse, and sodium alginate.

In some embodiments of the present invention, zolpidem or single stereoisomer, mixtures of stereoisomers, pharmaceutically acceptable salts or prodrugs thereof is formulated in the form of a nasal mucoadhesive in-situ gel. In some embodiments, the nasal mucoadhesive in-situ gel is fluid-like prior to the nasal administration, and once sprayed intranasally the phase transition of polymeric excipients is readily triggered by the environmental changes (for example, by ion concentration, pH, or temperature), resulting in viscous gel formation. Thus, the mucociliary clearance will be minimized and drug bioavailability is improved. In some embodiments, a polymeric excipient forming in-situ gel includes but is not limited to, carbomer, carrageenan, cellulose acetate phthalate, gellan gum, pectin, sodium alginate, poloxamer.

The present invention provides pharmaceutical compositions. In some embodiments a pharmaceutical composition comprises a compound having Formula I

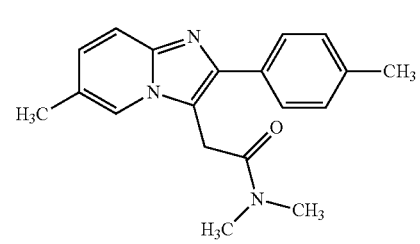

Formula I or a single stereoisomer, mixtures of stereoisomers, pharmaceutically acceptable salts or prodrugs thereof, HP-β-cyclodextrin, and at least one aqueous vehicle polymer capable of changing in a nasal fluid a theological behavior in relation to pH change, in relation to temperature change, or in the presence of ions.

The present invention provides pharmaceutical compositions. In some embodiments a pharmaceutical composition consists essentially of a compound having Formula I

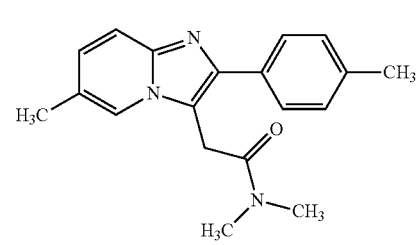

Formula I or a single stereoisomer, mixtures of stereoisomers, pharmaceutically acceptable salts or prodrugs thereof, HP-β-cyclodextrin, and at least one aqueous vehicle polymer capable of changing in a nasal fluid a rheological behavior in relation to pH change, in relation to temperature change, or in the presence of ions.

In some embodiments, the compound of formula I or a single stereoisomer, mixtures of stereoisomers, pharmaceutically acceptable salts or prodrugs thereof is at a concentration between about 5 mg/ml and about 100 mg/ml. In some embodiments, HP-13-cyclodextrin is at a concentration of about 50 mg/ml to about 600 mg/ml.

In some embodiments the pharmaceutical composition has a pH from about 3.0 to about 9.

In some embodiments, a pharmaceutical composition comprises an aqueous solvent vehicle suitable for intranasal spray using a spray device.

In some embodiments, a pharmaceutical composition comprises a bioadhesive polymeric material. In some embodiments, the bioadhesive polymer material is carboxymethylcellulose sodium. In some embodiments, the carboxymethylcellulose sodium is at a concentration of about 1 mg/ml to about 50 mg/ml.

In some embodiments, the bioadhesive polymer is hydroxypropyl methylcellulose. In some embodiments, the hydroxypropyl methylcellulose is at a concentration of about 1 mg/ml to about 50 mg/ml.

In some embodiments, the bioadhesive polymer is sodium alginate. In some embodiments, the sodium alginate is at a concentration of about 1 mg/ml to about 50 mg/ml.

In some embodiments, a pharmaceutical composition comprises a polymer capable of substantially lowering vehicle viscosity without any ion and substantially increasing the viscosity after intranasal administration of the pharmaceutical composition triggered by the ions in nasal. In some embodiments, such a polymer is selected from the group consisting of gellan gum and pectin. In some embodiments, the gellan gum is at a concentration of about 1 mg/ml to 20 mg/ml and the pectin is at a concentration of about 0.1 mg/ml to about 10 mg/ml.

In some embodiments, a pharmaceutical composition comprises a polymer capable of substantially lowering vehicle viscosity at room temperature and substantially increasing the viscosity after intranasal administration of the pharmaceutical composition triggered by a change in body temperature. In some embodiments, such a polymer is selected from the group consisting of Poloxamer407® and Poloxamer188®. In some embodiments, the Poloxamer407® is at a concentration of about 50 mg/ml to about 300 mg/ml and the Poloxamer188® is at a concentration of about 5 mg/ml to 50 mg/ml.

The present invention also provides various methods of using the compositions described herein. Provided are methods for treating an insomnia related disorder in a subject. In some embodiments, this method comprises the step of administering to a subject having an insomnia-related disorder or being at risk of developing an insomnia-related disorder a pharmaceutically effective amount of a composition comprising a compound having Formula I

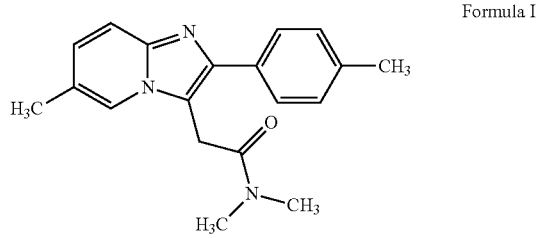

Formula I or a single stereoisomer, mixtures of stereoisomers, pharmaceutically acceptable salts or prodrugs thereof.

The present invention further provides kits, in particular intranasal spray application kits. In some embodiments of the present invention, such a kit comprises a compound having Formula I

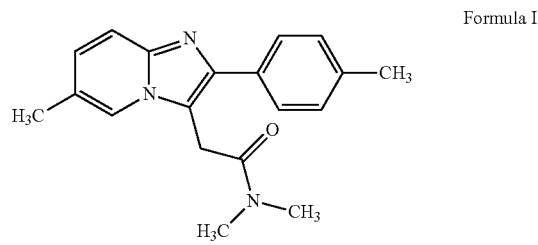

Formula I or a single stereoisomer, mixtures of stereoisomers, pharmaceutically acceptable salts or prodrugs thereof as an active ingredient in a pharmaceutically acceptable aqueous carrier and an actuation mechanism for providing a spray volume of about 0.05 to about 0.15 ml per actuation.

In some embodiments of the present invention, a kit consists essentially a compound having Formula I

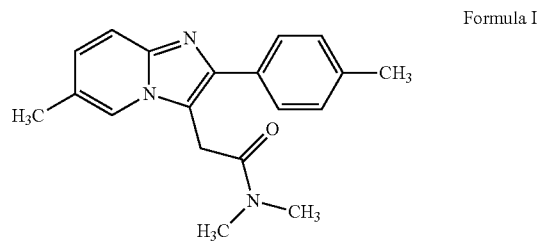

Formula I or a single stereoisomer, mixtures of stereoisomers, pharmaceutically acceptable salts or prodrugs thereof as an active ingredient in a pharmaceutically acceptable aqueous carrier and an actuation mechanism for providing a spray volume of about 0.05 to about 0.15 ml per actuation.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated herein and describe some preferred embodiments of the invention.

DETAILED DESCRIPTION OF THE INVENTION

I. Definitions

Figure 1:
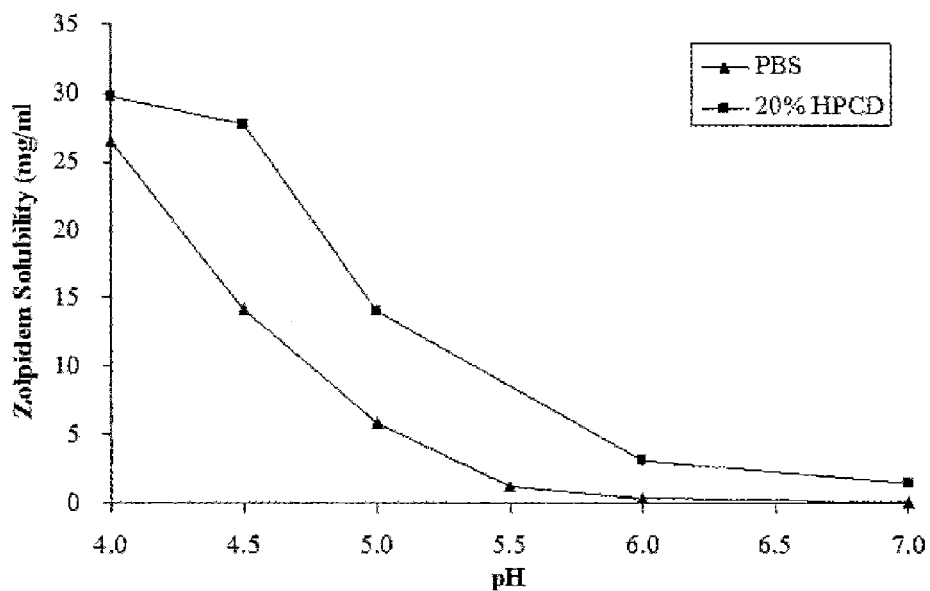
FIG. 1 schematically depicts zolpidem solubility in phosphate buffer saline (PBS) or 20% HP-β-CD aqueous solution at various pH levels. Details are described in Example 1.

Throughout the present specification and the accompanying claims the words "comprise," "include," "have" and variations thereof such as "comprises," "comprising," "includes," "including," "has," and "having" are to be interpreted inclusively. That is, these words are intended to convey the possible inclusion of other elements or integers not specifically recited, where the context allows. The term "consisting essentially of" means that the composition, method or structure may include additional ingredients, steps and/or parts, but only if the additional ingredients, steps and/or parts do not materially alter the basic and novel characteristics of the claimed composition, method or structure. No language in the specification should be construed as indicating any non-claimed element essential to the practice of the invention.

The terms "a" and "an" and "the" and similar referents used in the context of describing the invention (especially in the context of the following claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximate") one particular value, and/or to "about" (or "approximate") another particular value. When such a range is expressed, another embodiment includes from the one particular value and/or to the other particular value. Similarly, when values are expressed as approximations, by use of the antecedent "about" or "approximate" it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that is "less than or equal to the value" or "greater than or equal to the value" possible ranges between these values are also disclosed, as appropriately understood by the skilled artisan. For example, if the value "10" is disclosed the "less than or equal to 10" as well as "greater than or equal to 10" is also disclosed.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Units, prefixes, and symbols are denoted in their Système International de Unites (SI) accepted form.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); The Cambridge Dictionary of Science and Technology (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, the term "about" refers to a range of values of plus or minus 10% of a specified value. For example, the phrase "about 200" includes plus or minus 10% of 200, or from 180 to 220, unless clearly contradicted by context.

As used herein, the term "administering" means the actual physical introduction of a composition into or onto (as appropriate) a host or cell. Any and all methods of introducing the composition into the host or cell are contemplated according to the invention; the method is not dependent on any particular means of introduction and is not to be so construed. Means of introduction are well-known to those skilled in the art, and also are exemplified herein.

As used herein, the term "biological sample" refers to any sample obtained from a living or dead organism. Examples of biological samples include biological fluids specimens, such as blood, plasma, serum, sputum, tears, mucus, urine, saliva, oral fluid, nasal fluid, etc. Such samples are typically from humans, but include samples from non-human primates, or rodents, e.g., mice, and rats, canines, and other subjects. With respect to a "control sample," if, for example, a biological sample is obtained from a subject to whom a zolpidem composition of the present invention has been administered, then a control sample is a biological sample from a subject to whom another zolpidem composition has been administered or a biological sample from a subject to whom no zolpidem composition has been administered. "Providing a biological sample" means to obtain a biological sample for use in methods described in this invention. Most often, this will be done by removing a sample of cells from a subject, but can also be accomplished by using previously isolated samples (e.g., isolated by another person, at another time, and/or for another purpose), or by performing the methods of the invention in vivo. Archival tissues, having treatment or outcome history, will be particularly useful.

Synonyms of the terms "determining" or "determining the amount" or "determining the concentration" are contemplated within the scope of the present invention and include, but are not limited to, detecting, measuring, assaying, or testing the presence, absence, amount or concentration of a substance, a molecule, a metabolite, or a compound of the invention and the like. The term refers to both qualitative and quantitative determinations.

As used herein, "disorder", "disease" or "pathological condition" are used inclusively and refer to any deviation from the normal structure or function of any part, organ or system of the body (or any combination thereof). A specific disorder is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information. Preferred "disorders", "diseases" or "pathological conditions" amenable to prevention and/or treatment using compositions and methods described herein are insomnia as well as insomnia-related disorders as known in the art and recognized by one of ordinary skill in the art.

As used herein, the terms "dosage unit," or simply "dose" or "dosage" refer to discrete, predetermined quantities of a compound that can be administered as unitary dosages to a subject. A predetermined quantity of active compound can be selected to produce a desired therapeutic effect and can be administered with a pharmaceutically acceptable carrier. The predetermined quantity in each unit dosage can depend on factors that include, but are not limited to, (a) the unique characteristics of the active compound and the particular therapeutic effect to be achieved, and (b) the limitations inherent in the art of creating and administering such dosage units.

As used herein, the terms "effective amount", "effective dose", "sufficient amount", "amount effective to", "therapeutically effective amount," "pharmaceutically effective amount" or grammatical equivalents thereof mean a dosage sufficient to produce a desired result, to ameliorate, or in some manner, reduce a symptom or stop or reverse progression of a condition and provide either a subjective relief of a symptom(s) or an objectively identifiable improvement as noted by a clinician or other qualified observer. Amelioration of a symptom of a particular condition by administration of a pharmaceutical composition described herein refers to any lessening, whether permanent or temporary, lasting or transit that can be associated with the administration of the pharmaceutical composition.

The terms "individual," "subject," "host," and "patient," used interchangeably herein, refer to a mammal, including, but not limited to, murines, rats, simians, felines, canines, equines, bovines, mammalian farm animals, mammalian sport animals, and mammalian pets and humans. Preferred is a human.

As used herein, the term "insomnia" refers to a sleep disorder characterized by symptoms including, without limitation, difficulty in falling asleep, difficulty in staying asleep, intermittent wakefulness, and/or waking up too early. The term also encompasses daytime symptoms such as sleepiness, anxiety, impaired concentration, impaired memory, and irritability. Types of insomnia suitable for treatment with the compositions of the present invention include, without limitation, transient, short-term, and chronic insomnia. The term "transient insomnia" refers to insomnia lasting for a few nights. The term "short-term insomnia" refers to insomnia lasting for about two to about four weeks. The term "chronic insomnia" refers to insomnia lasting for at least one month.

Compounds that have the same molecular formula but differ in the nature or sequence of bonding of their atoms or the arrangement of their atoms in space are termed "isomers." Isomers that differ in the arrangement of their atoms in space are termed "stereoisomers." "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture." Unless otherwise indicated, the scope of the present invention includes individual enantiomers, racemates, diastereomers, tautomers, geometric isomers, and stereoisomers as well as mixtures of the compounds. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

The terms "optional" or "optionally" as used throughout the specification mean that the subsequently described event or circumstance may but need not occur, and that the description includes instances where the event or circumstance occurs and instances in which it does not. The terms also refer to a subsequently described composition that may but need not be present, and that the description includes instances where the composition is present and instances in which the composition is nor present.

As used herein, the term "oral fluid" means a biological fluid, such as saliva, gingival crevicular fluid and oral mucosal transudate obtained from an oral area of a subject.

As used herein, the term "pharmaceutically acceptable" or a grammatical equivalents thereof refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a Federal or state government or listed in the U.S. Pharmacopeia or other generally recognized pharmacopeia for use in animals, and more particularly in humans.

As used herein, the term "prodrug" refers to a compound, which is a drug precursor and which, following administration and absorption, releases the drug in vivo via some metabolic process. The term "prodrug" as used in this application also refers to a precursor or derivative form of a pharmaceutically active substance that is capable of being enzymatically activated or converted into the more active parent form. See, e.g., Wihnan, "Prodrugs in Cancer Chemotherapy" *Biochemical Society Transactions,* 14, pp. 375-382, 615th Meeting Belfast (1986) and Stella et al., "Prodrugs: A Chemical Approach to Targeted Drug Delivery," Directed Drug Delivery, Borchardt et al, (ed.), pp. 247-267, Humana Press (1985). Prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, (3-lactam-containing prodrugs, optionally substituted phenoxyacetamide-containing prodrugs or optionally substituted phenylacetamide-containing prodrugs, 5 fluorocytosine and other 5-fluorouridine prodrugs which can be converted into the more active drug.

As used herein, the terms "salt" and "pharmaceutically acceptable salt" refer to salts of a compound which is prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., 1977, "Pharmaceutical Salts", *Journal of Pharmaceutical Science*, 66:149). Certain specific compounds of the present invention contain both basic and acidic functionalities that allow the compounds to be converted into either base or acid addition salts. The neutral forms of a compound may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "sleep disorder" refers to a disruptive pattern of sleep arising from many causes including, without limitation, dysfunctional sleep mechanisms, abnormalities in physiological functions during sleep, abnormalities of the biological clock, and sleep disturbances that are induced by factors extrinsic to the sleep process. In particular, the term encompasses disorders associated with difficulties in staying asleep and/or falling asleep such as insomnia (e.g., transient, short-term, and chronic), delayed sleep phase syndrome, hypnotic-dependent sleep disorder, and stimulant-dependent sleep disorder; disorders associated with difficulties in staying awake such as sleep apnea, narcolepsy, restless leg syndrome, obstructive sleep apnea, central sleep apnea, idiopathic hypersomnia, respiratory muscle weakness-associated sleep disorder; disorders associated with difficulties in adhering to a regular sleep schedule such as sleep state misperception, shift work sleep disorder, chronic time zone change syndrome, and irregular sleep-wake syndrome; disorders associated with abnormal behaviors such as sleep terror disorder (i.e., parasomnia) and sleepwalking (i.e., somnambulism); and other disorders such as sleep bruxism, fibromyalgia, and nightmares.

As used herein, "subject" or "patient" to be treated for a pathological condition, disorder, or disease by a subject method means either a human or non-human animal in need of treatment for a pathological condition, disorder, or disease.

As used herein, the term "substantially lower," "substantially slower," or substantially decreased" and grammatical equivalents thereof refer to a level, amount, concentration of a parameter, such as a chemical compound, a metabolite, a nucleic acid, a polypeptide or a physical parameter (absorption, half life, pH, temperature, viscosity, etc.) measured in a sample, such as a biological sample, that has a decrease of at least 10%, preferably about 20%, more preferable about 40%, even more preferable about 50% and still more preferably a decrease of more than 75% when compared to the level, amount, or concentration of the same chemical compound, metabolite, nucleic acid, polypeptide or physical parameter in a control sample.

As used herein, the term "substantially faster, "substantially higher," or "substantially increased" and grammatical equivalents thereof refer to a level, amount, concentration of a parameter, such as a chemical compound, a metabolite, a nucleic acid, a polypeptide or a physical parameter (absorption, half life, pH, temperature, viscosity, etc.) measured in a sample, such as a biological sample, that has an increase of at least 30%, preferably about 50%, more preferable about 75%, and still more preferably an increase of more than 100% when compared to the level, amount, or concentration of the same chemical compound, metabolite, nucleic acid, polypeptide or physical parameter in a control sample.

As used herein, the terms "treatment", "treating" or grammatical equivalents thereof refer to both therapeutic treatment and prophylactic or preventative measures. Those in need of treatment include those already with the disease or disorder as well as those in which the disease or disorder is to be prevented. Hence, a subject may have been diagnosed as having the disease or disorder or may be predisposed or susceptible to the disease. As such, the terms include: (1) preventing a pathological condition, disorder, or disease, i.e. causing the clinical symptoms of a pathological condition, disorder, or disease not to develop in a subject that may be predisposed to the pathological condition, disorder, or disease but does not yet experience any symptoms of the pathological condition, disorder, or disease; (2) inhibiting the pathological condition, disorder, or disease, i.e. arresting or reducing the development of the pathological condition, disorder, or disease or its clinical symptoms; or (3) relieving the pathological condition, disorder, or disease, i.e. causing regression of the pathological condition, disorder, or disease or its clinical symptoms. These terms encompass also prophylaxis, therapy and cure. Treatment means any manner in which the symptoms of a pathological condition, disorder, or disease are ameliorated or otherwise beneficially altered. Preferably, the subject in need of such treatment is a mammal, more preferable a human.

II. Compositions

The present invention provides zolpidem compositions. In some embodiments of the present invention, a zolpidem composition described herein comprises zolpidem or single stereoisomers, mixtures of stereoisomers, pharmaceutically acceptable salts or prodrugs thereof. In some embodiments of the present invention, a zolpidem composition described herein consists essentially of zolpidem or single stereoisomers, mixtures of stereoisomers, pharmaceutically acceptable salts or prodrugs thereof. In some embodiments of the present invention, a zolpidem composition described herein consists of zolpidem or single stereoisomers, mixtures of stereoisomers, pharmaceutically acceptable salts or prodrugs thereof.

1. Pharmaceutically Acceptable Salts

Zolpidem can be used in a variety of forms in the methods of the present invention. In some embodiments, zolpidem is in the form of a free base or single stereoisomer, mixtures of stereoisomers, pharmaceutically acceptable salts or prodrugs thereof. A pharmaceutically acceptable salt includes, but is not limited to acetate, benzenesulfonate, benzoate, bicarbonate, bromide, calcium edentate, camsylate, carbonate, citrate, edetate, edisylate, estolate, esylate, fumarate, gluceptate, gluconate, glutamate, glycollylarsinate, hexylresorcinate, hydrabamine, hydrobromide, hydrochloride, hydroxynapthoate, iodide, isothionate, lactate, lactobionate, malate, maleate, mandelate, mesylate, methylbromide, methylnitrate, methylsulfate, mucate, napsylate, nitrate, pamoate, pantothenate, phosphate, polygalacturonate, salicylate, stearate, subacetate, succinate, sulfate, tartrate, teoclate, triethiodide.

In some embodiments of the present invention, a zolpidem composition comprises zolpidem tartrate. In some embodiments of the present invention, a zolpidera composition consists essentially of zolpidem tartrate. In some embodiments of the present invention, a zolpidem composition consists of zolpidem tartrate.

In some embodiments, zolpidem tartrate is formed between zolpidem and tartaric acid with a molar ratio of 2:1. In some embodiments, zolpidem tartrate is formed between zolpidem and tartaric acid with a molar ratio of 1:1. In some embodiments, zolpidem tartrate is formed between zolpidem and tartaric acid with a molar ratio of 1:2. In some embodiments, zolpidem tartrate is formed between zolpidem and tartaric acid with a molar ratio of between about 5:1 and about 2:1. In some embodiments, zolpidem tartrate is formed between zolpidem and tartaric acid with a molar ratio of between about 4:1 and about 2:1. In some embodiments, zolpidem tartrate is formed between zolpidem and tartaric acid with a molar ratio of between about 3:1 and about 2:1. In some embodiments, zolpidem tartrate is formed between zolpidem and tartaric acid with a molar ratio of between about 2:1 and about 5:1. In some embodiments, zolpidem tartrate is formed between zolpidem and tartaric acid with a molar ratio of between about 2:1 and about 4:1. In some embodiments, zolpidem tartrate is formed between zolpidem and tartaric acid with a molar ratio of between about 2:1 and about 3:1.

2. Doses and Dosage Units of Zolpidem Compositions

Zolpidem can be used in a variety of doses or dosage units in the methods of the present invention. In some embodiments of the present invention, the dose of zolpidem or single stereoisomer, mixtures of stereoisomers, pharmaceutically acceptable salts or prodrugs thereof ranges between about 0.1 mg and about 30 mg. In some embodiments of the present invention, the dose of zolpidem or single stereoisomer, mixtures of stereoisomers, pharmaceutically acceptable salts or prodrugs thereof ranges between about 0.5 and about 20 mg. In some embodiments of the present invention, the dose of zolpidem or single stereoisomer, mixtures of stereoisomers, pharmaceutically acceptable salts or prodrugs thereof ranges between about 2 and about 10 mg. In some embodiments of the present invention, the dose of zolpidem or single stereoisomer, mixtures of stereoisomers, pharmaceutically acceptable salts or prodrugs thereof ranges between about 2 and about 5 mg.

3. Forms of Zolpidem Compositions

The compositions may be in the form of a solution (aqueous or non-aqueous) or in form of a powder. In some embodiments of the present invention, a composition comprising zolpidem is an aqueous solution. In some embodiments of the present invention, a composition consisting essentially of zolpidem is an aqueous solution. In some embodiments of the present invention, a composition consisting of zolpidem is an aqueous solution. Aqueous solutions are preferred because of a rapid drug release as well as minimal nasal irritation.

In some embodiments of the present invention, an aqueous solution comprises zolpidem or single stereoisomer, mixtures of stereoisomers, pharmaceutically acceptable salts or prodrugs thereof in a concentration ranging from about 1 mg/ml to about 100 mg/ml. In some embodiments of the present invention, an aqueous solution comprises zolpidem or single stereoisomer, mixtures of stereoisomers, pharmaceutically acceptable salts or prodrugs thereof in a concentration ranging from about 5 mg/ml to about 50 mg/ml. In some embodiments of the present invention, an aqueous solution comprises zolpidem or single stereoisomer, mixtures of stereoisomers, pharmaceutically acceptable salts or prodrugs thereof in a concentration ranging from about 10 mg/ml to about 30 mg/ml. In some embodiments of the present invention, an aqueous solution consists essentially of zolpidem or single stereoisomer, mixtures of stereoisomers, pharmaceutically acceptable salts or prodrugs thereof in a concentration ranging from about 1 mg/ml to about 100 mg/ml. In some embodiments of the present invention, an aqueous solution consists essentially of zolpidem or single stereoisomer, mixtures of stereoisomers, pharmaceutically acceptable salts or prodrugs thereof in a concentration ranging from about 5 mg/ml to about 50 mg/ml. In some embodiments of the present invention, an aqueous solution consists essentially of zolpidem or single stereoisomer, mixtures of stereoisomers, pharmaceutically acceptable salts or prodrugs thereof in a concentration ranging from about 10 mg/ml to about 30 mg/ml. In some embodiments of the present invention, an aqueous solution consists of zolpidem or single stereoisomer, mixtures of stereoisomers, pharmaceutically acceptable salts or prodrugs thereof in a concentration ranging from about 1 mg/ml to about 100 mg/ml. In some embodiments of the present invention, an aqueous solution consists of zolpidem or single stereoisomer, mixtures of stereoisomers, pharmaceutically acceptable salts or prodrugs thereof in a concentration ranging from about 5 mg/ml to about 50 mg/ml. In some embodiments of the present invention, an aqueous solution consists of zolpidem or single stereoisomer, mixtures of stereoisomers, pharmaceutically acceptable salts or prodrugs thereof in a concentration ranging from about 10 mg/ml to about 30 mg/ml.

4. Spray Volumes

Various spray volumes of an aqueous solution of a zolpidem composition described herein can be used to practice methods of the invention. In some embodiments, the spray volume ranges from about 10 μL to about 200 μL. In some embodiments, the spray volume ranges from about 20 μL to about 50 μL. In some embodiments, the spray volume ranges from about 50 μL to about 100 μL per nostril.

5. Solubilizing Agents

Zolpidem tartrate is slightly soluble in water (British Pharmacopeia 2009, Merck Index, 13th Edition). The aqueous solubility is about 23 mg/ml at 20° C. As a weak base with $pK_a$ of 6.16, aqueous solubility of zolpidem dramatically decreases when pH increases greater than 4.5. Various solubilizing agents have been incorporated in the solution when making the nasal formulation allowing zolpidem concentration being high enough without compromising its solubility to provide therapeutic effects. Preferred solubilizing agents include, but are not limited to: (1) cyclodextrins, i.e. methyl-β-cyclodextrin, HP-β-cyclodextrin, and SBE-β-cyclodextrin; (2) surfactants, i.e. Tween20®, Tween80®, CremophorEL®, SolutolHS15®; PluronicF68® and PluronicF127®; (3) organic solvents, i.e. ethanol, propylene glycol, glycerol, glycofurol, glycerin; and (4) hydrophilic polymers, i.e. polypovidone, PEG400, carboxymethylcellulose sodium. These solubilizing agents have been approved by FDA as pharmaceutical excipients with high safety profile, and have been applied in nasal, ophthalmic, oral, or injectable formulations, to enhance solubility of poorly soluble drugs. Each of those solubilizing agents may be used in compositions and methods of the present invention. Thus, in some embodiments a zolpidem composition comprises a cyclodextrin. In some embodiments of the present invention, the solubilizing agent is methyl-β-cyclodextrin. In some embodiments of the present invention, the solubilizing agent is HP-β-cyclodextrin. In some embodiments of the present invention, the solubilizing agent is SBE-β-cyclodextrin. In some embodiments a zolpidem composition comprises a surfactant. In some embodiments a zolpidem composition comprises an organic solvent. In some embodiments a zolpidem composition comprises a hydrophilic polymer.

6. Polymer with Bioadhesive Property

In some embodiments of the present invention, a zolpidem composition comprises one or more aqueous soluble polymers with a bioadhesive property. Those polymers can be adhesive substances produced by or obtained from living organisms, or used on living tissue. In some embodiments of the present invention, a zolpidem composition comprises zolpidem tartrate and one or more aqueous soluble polymers with a bioadhesive property.

An aqueous soluble polymer with bioadhesive property reduces mucocilliary clearance (MCC). A zolpidem composition comprising one or more aqueous soluble polymers with a bioadhesive property has a prolonged drug residence time intranasally as well as an improved rate and extent of drug absorption (e.g., see Examples 10 and 11). In some embodiments, the prolonged drug residence time intranasally (which may also be referred to as half life or nasal residence time) is more than 30 minutes. In some embodiments, the prolonged drug residence time intranasally is more than 40 minutes. In some embodiments, the prolonged drug residence time intranasally is more than 50 minutes. In some embodiments, the prolonged drug residence time intranasally is more than 60 minutes. In some embodiments, the prolonged drug residence time intranasally is more than 70 minutes. In some embodiments, the prolonged drug residence time intranasally is more than 80 minutes. In some embodiments, the prolonged drug residence time intranasally is more than 90 minutes. In some embodiments, the prolonged drug residence time intranasally is more than 2 hours. In some embodiments, the prolonged drug residence time intranasally is more than 3 hours.

In some embodiments of the present invention, a zolpidem composition, preferably a zolpidem tartrate composition is mixed with a polymeric bioadhesive material selected from the group consisting of acacia, albumin, carboxymethylcellulose sodium, carrageenan, cellulose microcrystalline, cellulose acetate, chitosan, dextrin, gelatin, guar gum, hyaluronic acid, hydroxylethylcellulose, hydroxypropyl starch, hydroxypropylcellulose, hydroxymethylpropylcelloluse, methyl cellulose, polyethylene glycols, poly(methyl vinyl ether/maleic anhydride), povidone, rafinose, shellac, sodium alginate, sodium starch glycolate, starch and pregelatinized starch, tragacanth, and xanthan. In some embodiments, the polymeric bioadhesive material selected from the group consisting of carboxymethylcellulose, carrageenan, sodium, hyaluronic acid, and hydroxymethylpropylcelloluse. In some embodiments, the polymeric bioadhesive material is carboxymethylcellulose. In some embodiments, the polymeric bioadhesive material is carrageenan. In some embodiments, the polymeric bioadhesive material is sodium. In some embodiments, the polymeric bioadhesive material is hyaluronic acid. In some embodiments, the polymeric bioadhesive material is hydroxymethylpropylcelloluse.

7. In-Situ Gel Formulations

Some disadvantages of bioadhesive formulations of the prior art include a high viscosity and the difficulty in intranasal application. The present invention overcomes those disadvantages by providing zolpidem compositions formulated as an in-situ gel. Different from the viscous solutions of the prior art containing bioadhesive polymers, the zolpidem solutions of in-situ gel formula exhibit low viscosity under general storage conditions. Viscosity, according to the International System of Units is given as Pa·s (Pascal second). In some embodiments, the viscosity is less than 1 Pa·s. In some embodiments, the viscosity is less than 2 Pa·s. In some embodiments, the viscosity is less than 5 Pa·s. In some embodiments, the viscosity is less than 10 Pa·s. In some embodiments, the viscosity is less than 15 Pa·s. In some embodiments, the viscosity is less than 20 Pa·s. In some embodiments, the viscosity is about 1 Pa·s. In some embodiments, the viscosity is about 2 Pa·s. In some embodiments, the viscosity is about 5 Pa·s. In some embodiments, the viscosity is about 10 Pa·s. In some embodiments, the viscosity is about 10 Pa·s. In some embodiments, the viscosity is about 20 Pa·s. In some embodiments, the viscosity is between about 1 Pa·s and 20 Pa·s. In some embodiments, the viscosity is between about 2 Pa·s and 15 Pa·s. In some embodiments, the viscosity is between about 5 Pa·s and about 10 Pa·s. In some embodiments, general storage condition comprises storing a zolpidem composition of the present invention in a plastic or glass container. In some embodiments, general storage condition comprises storing a zolpidem composition of the present invention at room temperature.

In addition, the in-situ gel is readily formed upon nasal administration as a result of the changing environment in the nasal cavity, i.e. temperature, pH, or ion concentration. Thus, the low viscosity solutions of the present invention can be easily and accurately applied using a nasal spray device. Upon contacting nasal mucosa, the in-situ gel provides a prolonged nasal residence time (see above) as compared to the conventional liquid formulations, which typically have a half-life of less than 30 minutes, some even less than 15 minutes). As such, zolpidem composition of the present invention provide an unexpected and surprising advantage over the prior art zolpidem compositions.

Polymers suitable for in-situ gel formulations include, but are not limited to, carbomer, carrageenan, cellulose acetate phthalate, gellan gum, pectin, sodium alginate, poloxamer. Thus, in some embodiments of the present invention, a zolpidem composition comprises a polymer selected from the group consisting of carbomer, carrageenan, cellulose acetate phthalate, gellan gum, pectin, sodium alginate, and poloxamer. In some embodiments of the present invention, a zolpidem composition comprises a polymer selected from the group consisting of carbomer, gellan gum, and pectin. In some embodiments of the present invention, the polymer is carbomer. In some embodiments of the present invention, the polymer is gellan gum. In some embodiments of the present invention, the polymer is pectin.

8. Pharmaceutically Acceptable Buffering Agent

In some embodiments of the present invention, a zolpidem composition of the present invention includes a pharmaceutically acceptable buffering agent. A pharmaceutically acceptable buffering agent is included to maintain an optimal pH condition for achieving physicochemical stability and minimizing local irritation to nasal mucosa. According to the present invention, in some embodiments, the pH range of a zolpidem composition ranges from about 3.0 to about 9.0. In some embodiments, the pH range of a zolpidem composition ranges from about 4.0 to about 7.0. Suitable buffering systems include, but not limited to, acetic buffer, boric buffer, citrate buffer, phosphate buffer, tartaric buffer, and tris buffer.

9. Pharmaceutical Preservative

Zolpidem compositions of the present invention may optionally include a pharmaceutical preservative. A pharmaceutical preservative may be added to a zolpidem composition to maintain microbiological stability. Suitable preservatives include, but are not limited to, benzalkonium chloride, benzethonium chloride, benzyl alcohol, chlorobutanol, chlorhexidine, methylparaben and propylparaben, phenylethyl alcohol, phenylmercuric acetate, and thimerosal. A pharmaceutical preservative has no adverse effect on cilli. Thus, in some embodiments of the present invention, a zolpidem composition comprises a pharmaceutical preservative selected from the group consisting of benzalkonium chloride, benzethonium chloride, benzyl alcohol, chlorobutanol, chlorhexidine, methylparaben and propylparaben, phenylethyl alcohol, phenylmercuric acetate, and thimerosal. In some embodiments, the pharmaceutical preservative is benzyl alcohol. In some embodiments, the pharmaceutical preservative is chlorhexidine. In some embodiments, the pharmaceutical preservative is thimerosal.

10. Optional Components

A zolpidem composition of the present invention may optionally contain one or more of the following: (1) a chelator, e.g., sodium EDTA; (2) an antioxidant, e.g., sodium metabisulphite; (3) a tonicity agent, including, but not limited to, dextrose, glycerin, hydroxypropyl betadex, mannitol, potassium chloride, and sodium chloride; (4) an absorption enhancer including without limitation, a bile salt, a cyclodextrin, a fatty acid, a fusidic acid derivative, a phosphatidylcholine, Laureth-9, an oleic acid, a surfactant, etc. (Davis, Stanley S; Illum, Lisbeth. Absorption enhancers for nasal drug delivery. *Clin Pharmacokinet* 2003; 42(13):1107-28).

III. Methods

The present invention provides methods using the zolpidem compositions described herein. As one of ordinary skill in the art will appreciate the zolpidem compositions can be used in various methods. As a non-limiting use of the zolpidem compositions described herein, the present invention provides a method of administering a pharmaceutically effective amount of a zolpidem composition to a subject in need thereof. In some embodiments of this method, the method comprises the step of spraying the pharmaceutically effective amount of the zolpidem composition into a nasal cavity or nostril of the subject. Preferably, the zolpidem composition is in solution form. In some embodiments, the zolpidem composition is within a non-pressurized dispenser. Suitable dispensers include, but are not limited to, a spray pump and a bottle. In some embodiments, a single dose is delivered to the subject. In some embodiments, multiple doses are delivered to the subject. Doses may be delivered to the subject by mechanical actuation. Various spray volumes can be used to practice the method. In some embodiments, the spray volume ranges from about 10 μL to about 200 μL per nasal cavity or nostril. In some embodiments, the spray volume ranges from about 20 μL to about 50 μL per nasal cavity or nostril. In some embodiments, the spray volume ranges from about 50 μL, to about 100 μL per nasal cavity or nostril.

The zolpidem compositions of the present invention administrated intranasally to a subject can induce rapid sleeping effects. Thus, the present invention also provides methods for the treatment of insomnia and an insomnia-related disorder. An insomnia-related disorder includes, but is not limited to, a difficulty with sleep initiation or middle of the night awakening. In some embodiments of the method for treatment of an insomnia-related disorder, the method comprises the step of administering a pharmaceutically effective amount of a zolpidem composition to a subject in need thereof. A subject in need thereof is a subject having an insomnia-related disorder or a subject being at risk of developing an insomnia-related disorder. In some embodiments of this method, the method comprises the step of spraying the pharmaceutically effective amount of the zolpidem composition into a nasal cavity or nostril of the subject. Preferably, the zolpidem composition is in solution form. In some embodiments, the zolpidem composition is within a non-pressurized dispenser. Suitable dispensers include, but are not limited to, a spray pump and a bottle. In some embodiments, a single dose is delivered to the subject. In some embodiments, multiple doses are delivered to the subject. Doses may be delivered to the subject by mechanical actuation. Various spray volumes can be used to practice the method. In some embodiments, the spray volume ranges from about 10 μL to about 200 μL per nasal cavity or nostril. In some embodiments, the spray volume ranges from about 20 μL to about 50 μL per nasal cavity or nostril. In some embodiments, the spray volume ranges from about 50 μL to about 100 μL per nasal cavity or nostril.

In some embodiments, the method comprises the step of selecting a subject suffering from insomnia or suffering from an insomnia-related disorder as described herein. A qualitative measure of insomnia includes, but is not limited to, a subjective estimation of sleep quality e.g., poor to excellent or as on a Likert scale of 1 to 10. A quantitative measure of insomnia includes, but is not limited to, the Insomnia Severity Index (ISI) score, subjective and objective estimates of Sleep Onset Latency, Wake After Sleep Onset, and Snooze time. Such quantitative measures of insomnia may be compared to a standard threshold, e.g., the Sleep Onset Latency threshold is set to 30 minutes. Such a comparison may be used to assess the type of sleep disturbance (problem with sleep initiation, sleep maintenance or early awakenings, etc.). Further, subjective and objective estimates of Sleep Efficiency, may be compared to standard thresholds (e.g., 90%) to assess whether or not the patient sleeps in a consolidated way.

Compositions of the present invention can be used to treat insomnia and insomnia-related disorders. In some embodiments the insomnia is a chronic insomnia. In some embodiments, the insomnia is a non-chronic insomnia. For chronic (e.g., greater than 3-4 weeks) or non-chronic insomnias, a patient may suffer from difficulties in sleep onset, sleep maintenance (interruption of sleep during the night by periods of wakefulness), sleep duration, sleep efficiency, premature early-morning awakening, or a combination thereof. Also, the insomnia may be attributable to the concurrent use of other medication. The non-chronic insomnia can be, for example, a short term insomnia or a transient insomnia. The chronic or non-chronic insomnia can be a primary insomnia or an insomnia that is secondary to another condition, for example a disease such as depression or chronic fatigue syndrome. In some aspects, the patient can be one that is not suffering from an insomnia that is a component of a disease, or a patient can be treated that is otherwise healthy. As previously mentioned, the chronic or non-chronic insomnia can be a primary insomnia, that is, one that is not attributable to another mental disorder, a general medical condition, or a substance. In many cases, such conditions may be an insomnia-related disorder and associated with a chronic insomnia and can include, but are not limited to, insomnia attributable to a diagnosable DSM-IV disorder, a disorder such as anxiety or depression, or a disturbance of the physiological sleep-wake system. In some aspects the insomnia can be non-chronic, or of short duration (e.g., less than 3-4 weeks). Examples of causes of such insomnia may be extrinsic or intrinsic and include, but are not limited to, environmental sleep disorders as defined by the International Classification of Sleep Disorders (ICSD) such as inadequate sleep hygiene, altitude insomnia or adjustment sleep disorder (e.g., bereavement). Also, short-term insomnia may also be caused by disturbances such as shift-work sleep disorder.

In some embodiments of the present invention, a composition of the present invention is used to treat diverse neuropsychiatric disorders, each of which may have insomnia as a contributing component or which may be characterized by its own abnormal pattern of cerebral metabolism. In some embodiments, an insomnia-related disorder is a neuropsychiatric disorder. Neuropsychiatric disorders include, but are not limited to, depression, chronic pain, headache, migraine, fibromyalgia, arthritis (osteoarthritis, rheumatoid arthritis and autoimmune diseases such as lupus), and post-traumatic stress disorder (PTSD).

The present invention also provides methods for the treatment of a sleep disorder. In some embodiments of the method for treatment of a sleep disorder, the method comprises the step of administering a pharmaceutically effective amount of a zolpidem composition to a subject in need thereof. A subject in need thereof is a subject having a sleep disorder or a subject being at risk of developing a sleep disorder. In some embodiments of this method, the method comprises the step of spraying the pharmaceutically effective amount of the zolpidem composition into a nasal cavity or nostril of the subject.

In some embodiments of methods of the present invention the efficacy of administering a zolpidem composition to a subject in need thereof comprises determining the presence or absence of a zolpidem metabolite in a biological sample obtained from the subject treated. In some embodiments, this step comprises determining the concentration of a zolpidem metabolite in a biological sample obtained from the subject treated. In some embodiments, a method of the present invention comprises the step of providing a biological sample from the subject. A preferred biological sample is a fluid nasal sample. Another preferred sample is an oral fluid sample.

Figure 6:
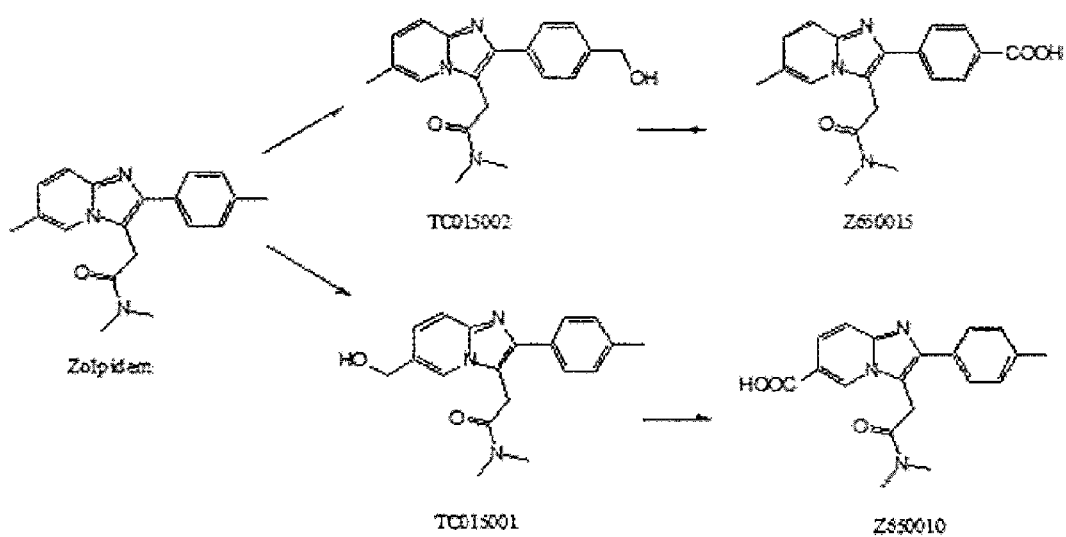
FIG. 6 shows zolpidem and its metabolites in Beagle dogs.

In some embodiments, a zolpidem metabolite is selected from the group consisting of TC015002, TC015001, Z650015 and Z650010. In some embodiments, the zolpidem metabolite is TC015002. In some embodiments, the zolpidem metabolite is TC015001. In some embodiments, the zolpidem metabolite is Z650015. In some embodiments, the zolpidem metabolite is Z650010. Zolpidem metabolites are schematically shown in FIG. 6.

In some embodiments of the present invention, determining the absence, presence and, in particular, the concentration of one or more zolpidem metabolites is used to indicate the minimized first pass effect from an oral route after administration of the zolpidem composition.

Determining the absence, presence, in particular the concentration of a zolpidem metabolite in a biological sample obtained from a subject treated with a zolpidem composition of the present invention and comparing the data obtained to the data obtained from another subject treated with a prior art zolpidem composition shows the superiority and advantages of the zolpidem compositions of the present invention. Those advantages, as described herein, include, e.g., a substantially faster onset of sedative effects, a substantially prolonged drug residence time (i.e., substantially longer half life), a substantially improved rate and extent of drug absorption, and a substantially lower viscosity.

In some embodiments of methods of the present invention the efficacy of administering a zolpidem composition of the present ion to a subject in need thereof comprises determining one or more of a zolpidem metabolite. In some embodiments, this step comprises determining the presence or absence of a zolpidem metabolite in a biological sample obtained from the subject treated. In some embodiments, this step comprises determining the concentration of a zolpidem metabolite in a biological sample obtained from the subject treated.

Any of the methods and compositions described herein may be used to treat insomniacs, however these methods and compositions may also be used to generally improve healthy sleep, even in non-insomniac subjects. In particular, these methods and compositions may be used to improve sleep in individuals who experience sleeplessness.

Further, the methods and compositions described herein may be used as part of a method to treat and improve sleep in individuals with neuropsychiatric disorders such as, but not limited to, depression, mood disorders, anxiety disorders, substance abuse, post-traumatic stress disorder, psychotic disorders, manic-depressive illness and personality disorders and any neuropsychiatric patient who experiences sleeplessness.

Preferred embodiments of this invention are described herein, including the best mode known to the inventors for carrying out the invention. Of course, variations, changes, modifications and substitution of equivalents on those preferred embodiments will become apparent to those of ordinary skill in the art upon reading the foregoing description. The inventors expect skilled artisans to employ such variations, changes, modifications and substitution of equivalents as appropriate, and the inventors intend for the invention to be practiced otherwise than specifically described herein. Those of skill in the art will readily recognize a variety of non-critical parameters that could be changed, altered or modified to yield essentially similar results. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The below examples are meant to illustrate specific embodiments of the methods and compositions described herein and are not intended nor should they be construed as limiting the definition or scope of the invention in any way.

IV. Examples

Although preferred embodiment described herein are in reference to zolpidem tartrate, as one of ordinary skill in the art will appreciate, other suitable hypnotics and their salts/complexes may also provide satisfactory results.

Example 1

Solubility Measurement

Figure 2:
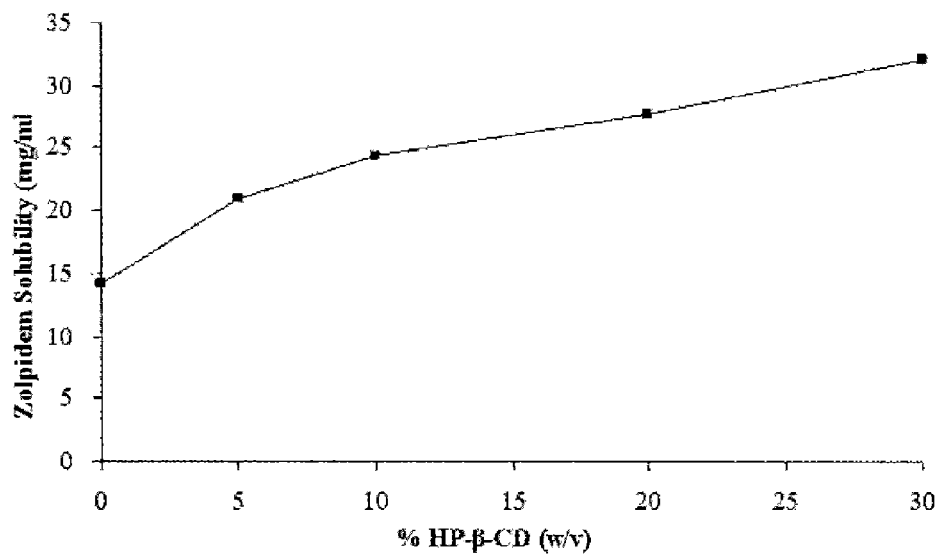
FIG. 2 schematically depicts zolpidem solubility in different concentrations of HP-β-cyclodextrin aqueous solution (pH 4.5). Details are described in Example 1.

Solubility of zolpidem tartrate under various conditions (as noted in FIG. 1 and FIG. 2) was measured at room temperature using the "shake flask" method. Briefly, excess amount of zolpidem tartrate was added into a glass beaker containing 5 ml solvent under intense stirring for 1 hour, then placed into a shaking water bath, mixing at 100 rpm for 24 hours, the suspensions were then filtrated through 0.45-micron syringe filter to obtain the clear and saturated solutions. The pH values of these solutions were measured and recorded. 80 μl of the saturated solution was diluted to 100 ml using deionized water immediately. The zolpidem content in the diluted solution was measured using a DU-800 UV spectrophotometer (Beckman Coulter) at the wavelength of 292 nm. The results were summarized in FIG. 1 and FIG. 2. Zolpidem solubility at various pH levels in phosphate buffer saline (PBS) versus 20% HP-β-CD aqueous solution is shown in FIG. 1. Zolpidem solubility in pH 4.5 and at different concentration of HP-β-cyclodextrin aqueous solution is shown in FIG. 2.

Example 2

Formulation I (ZLP-B01)

This example describes the process of preparing a bioadhesive formulation containing 18 mg/ml zolpidem tartrate and hydroxymethylpropylcellulose (HPMC) for intranasal administration in accordance with the invention. The particular formulation is detailed in Table 1.

TABLE 1

| Composition | Amount (for 10 L) |
| --- | --- |
| Zolpidem tartrate | 180 g |
| HP-β-Cyclodextrin | 2000 g |
| HPMC | 25 g |
| Benzyl alcohol | 50 ml |
| Purified water | q.s. to 10 L |

Preparation Process:
(a) charge zolpidem tartrate, HP-β-cyclodextrin, HPMC, and benzyl alcohol in a stainless steel equipped with mixer, introduce about 8 L purified water and mix until all materials are dissolved;

(b) add the purified water to the required volume (10 L);
(c) check and adjust the solution pH to 4.6-4.9 by HCl or NaOH;
(d) filter the solution through a 0.45-micron filter; and
(e) fill the solution into a spray nasal dispenser with a volume of 3.5 nil and the applicator delivers a quantity comprising 1.8 mg Zolpidem Tartrate per actuation (0.1 ml).

Example 3

Formulation II (ZLP-B02)

This example describes the process of preparing a bioadhesive formulation containing 18 mg/ml zolpidem tartrate and carboxymethylcellulose sodium (CMCNa) for intranasal administration in accordance with the invention. The particular formulation is detailed in Table 2.

TABLE 2

| Composition | Amount (for 10 L) |
| --- | --- |
| Zolpidem tartrate | 180 g |
| HP-β-Cyclodextrin | 2000 g |
| CMCNa | 50 g |
| Benzyl alcohol | 50 ml |
| Purified water | q.s. to 10 L |

Preparation Process:
(a) charge zolpidem tartrate, HP-β-cyclodextrin, CMCNa, and benzyl alcohol in a stainless steel equipped with mixer, introduce about 8 L purified water and mix until all materials are dissolved;
(b) add the purified water to the required volume (10 L);
(c) check and adjust the solution pH to 4.6-4.9 by HCl or NaOH;
(d) filter the solution through a 0.45-micron filter; and
(e) fill the solution into a spray nasal dispenser with a volume of 3.5 ml and the applicator delivers a quantity comprising 1.8 mg zolpidem tartrate per actuation (0.1 ml).

Example 4

Formulation III (ZLP-B03)

This example describes the process of preparing a bioadhesive formulation containing 18 mg/ml zolpidem tartrate and sodium alginate for intranasal administration in accordance with the invention. The particular formulation is detailed in Table 3.

TABLE 3

| Composition | Amount (for 10 L) |
| --- | --- |
| Zolpidem tartrate | 180 g |
| HP-β-Cyclodextrin | 2000 g |
| Sodium Alginate | 100 g |
| Benzyl alcohol | 50 ml |
| Purified water | q.s. to 10 L |

Preparation Process:
(a) charge zolpidem tartrate, HP-β-cyclodextrin, sodium alginate, and benzyl alcohol in a stainless steel equipped with mixer, introduce about 8 L purified water and mix until all materials are dissolved;
(b) add the purified water to the required volume (10 L);
(c) check and adjust the solution pH to 4.6-4.9 by HCl or NaOH;

(d) filter the solution through a 0.45-micron filter;
(e) fill the solution into a spray nasal dispenser with a volume of 3.5 ml and the applicator delivers a quantity comprising 1.8 mg zolpidem tartrate per actuation (0.1 ml).

Example 5

Formulation IV (ZLP-I01)

This example describes the process of preparing an ion-sensitive in-situ gel formulation containing 18 mg/ml zolpidem tartrate and gellan gum for intranasal administration in accordance with the invention. The particular formulation is detailed in Table 4.

TABLE 4

| Composition | Amount (for 10 L) |
| --- | --- |
| Zolpidem tartrate | 180 g |
| HP-β-Cyclodextrin | 1500 g |
| Gellan Gum | 50 g |
| Benzyl alcohol | 50 ml |
| Purified water | q.s. to 10 L |

Preparation Process:
(a) charge zolpidem tartrate and HP-β-cyclodextrin in a stainless steel equipped with mixer and a heating sleeve, introduce about 8 L purified water and mix until all materials are dissolved;
(b) add gellan gum under constant stirring and heat to 80° C. until gellan gum is completely dissolved;
(c) cool the solution to room temperature and introduce benzyl alcohol by stirring;
(d) add the purified water to the required volume (10 L);
(e) check and adjust the solution pH to 4.6-4.9 by HCl or NaOH;
(f) filter the solution through a 0.45-micron filter; and
(g) fill the solution into a spray nasal dispenser with a volume of 3.5 ml and the applicator delivers a quantity comprising 1.8 mg zolpidem tartrate per actuation (0.1 ml).

Example 6

Formulation V (ZLP-I02)

This example describes the process of preparing a temperature-sensitive in-situ gel formulation containing 18 mg/ml zolpidem tartrate and poloxamer for intranasal administration in accordance with the invention. The particular formulation is detailed in Table 5.

TABLE 5

| Composition | Amount (for 10 L) |
| --- | --- |
| Zolpidem tartrate | 180 g |
| Poloxamer407 ® | 1800 g |
| Poloxamer188 ® | 100 g |
| Benzyl alcohol | 50 ml |
| 0.05N HCL | q.s. 10 L |

Preparation Process:
(a) charge zolpidem tartrate and benzyl alcohol in a stainless steel equipped with mixer, introduce about 7.6 L 0.05N HCl and keep stirring at the room temperature until obtaining a clear solution;
(b) add Poloxamer188® into the above solution and stir, after dissolve completely, add Poloxamer407® into the solution and stir for 5 minutes, and then add the rest HCl to the metered amount;
(c) place the solution at 4° C. until obtain a clear solution (overnight);
(d) filter the solution through a 0.45-micron filter; and
(e) fill the solution into a spray nasal dispenser with a volume of 3.5 ml and the applicator delivers a quantity comprising 1.8 mg zolpidem tartrate per actuation (0.1 ml).

Example 7

Formulation VI (ZLP-I03)

This example describes the process of preparing another temperature-sensitive in-situ gel formulation containing 18 mg/ml zolpidem tartrate and poloxamer for intranasal administration in accordance with the invention without limiting the scope. The particular formulation is detailed in Table 6.

TABLE 6

| Composition | Amount (for 10 L) |
| --- | --- |
| Zolpidem tartrate | 180 g |
| HP-β-Cyclodextrin | 1600 g |
| Poloxamer407 ® | 1800 g |
| Poloxamer188 ® | 100 g |
| Benzyl alcohol | 50 ml |
| 0.1N HCL | q.s. 10 L |

Preparation Process:
(a) prepare 20% HP-β-cyclodextrin in purified water;
(b) charge zolpidem tartrate in a stainless steel equipped with mixer, and 5.2 L 20% HP-β-cyclodextrin solution and stir for 10 minutes, then introduce 2 L 0.1N HCL and keep stirring at the room temperature until obtaining a clear solution;
(c) add Poloxamer188® into the above solution and stir, after dissolve completely, add Poloxamer407® into the solution and stir for 5 minutes, and then add the rest 20% HP-β-cyclodextrin solution to the metered amount;
(d) place the sample at 4° C. until obtain a clear solution (overnight);
(e) filter the solution through a 0.45-micron filter; and
(f) fill the solution into a spray nasal dispenser with a volume of 3.5 ml and store below 25° C.

Example 8

Viscosity of Formulation IV (ZLP-I01)

The viscosity of zolpidem composition formulation IV has been determined and is shown in Table 7.

TABLE 7

| | Viscosity (Pas) | |
| --- | --- | --- |
| Shear Rate (1/s) | ZLP-I01 | ZLP-I01 mixed with artificial nasal fluid* at 1:1 |
| 0.1 | 2.69 ± 0.76 | 23.23 ± 3.10 |

*Nasal fluid contains $Na^+$: 150 ± 32 mmol/L, $K^+$: 41 ± 18 mmol/L, $Ca^+$: 8 ± 4 mmol/L Example 9

Sol-Gel Transition Temperature

The physicochemical properties of two temperature-sensitive in-situ gel formulations (Formulation V and Formulation VI above) were measured. The results are shown in Table 8.

TABLE 8

| Formulation | Sol-gel transition temperature (° C.) | pH | Complex viscosity (Pa·S) | |
|---|---|---|---|---|
| | | | 20° C. | 35° C. |
| V | 32.69 | 2.86 | 0.0643 | 1151 |
| VI | 34.15 | 4.06 | 0.2371 | 453 |

Example 10

Pharmacokinetic Study in Rabbits

Pharmacokinetic study on intranasal absorption of zolpidem formulations was carried out in rabbits. An open labeled, single dose, 4-treatment, 2-group, 4-period crossover design was conducted. Eight New Zealand white rabbits (4 male and 4 female, aged 6-8 months, weighing 3-4 kg) were used in this study. Prior to administration of the zolpidem composition, the rabbits were restrained in an animal cage, and a catheter was placed in the rabbit's median ear artery to allow withdraw of multiple blood samples throughout the experiments. Heparin (50 IU/ml) at 0.1 ml was left in each catheter to prevent clotting of the line. For intranasal administration, 0.1 ml of zolpidem nasal solution (ZLP-B01) or nasal in-situ gel (ZLP-I01) was directly sprayed into each nostril of the rabbits using a nasal spray pump (Pfeiffer, model for infant use). The final dose for intranasal spray was 1.5 mg per rabbit. For oral administration, the rabbits were fasted overnight prior to the study and 2 ml zolpidem oral solution (ZLP-S04; Dose: 1.5 mg per rabbit) was administered via a soft plastic gavage, following by 3 ml of purified water. For intravenous administration, 0.5 ml I.V. solution (Dose: 1.5 mg per rabbit) was directly injected into the ear artery from the catheter. Each treatment was separated by a 1-week wash-out. Multiple blood samples were collected at pre-dose (0 min) and then at 3, 6, 10, 15, 20, 30, 45, 60, 90, 120, 180, and 240 min post dose. Zolpidem concentration in rabbit plasma was determined using a validated HPLC method. The standard non-compartmental method was used to determine the pharmacokinetic parameters.

Figure 3:
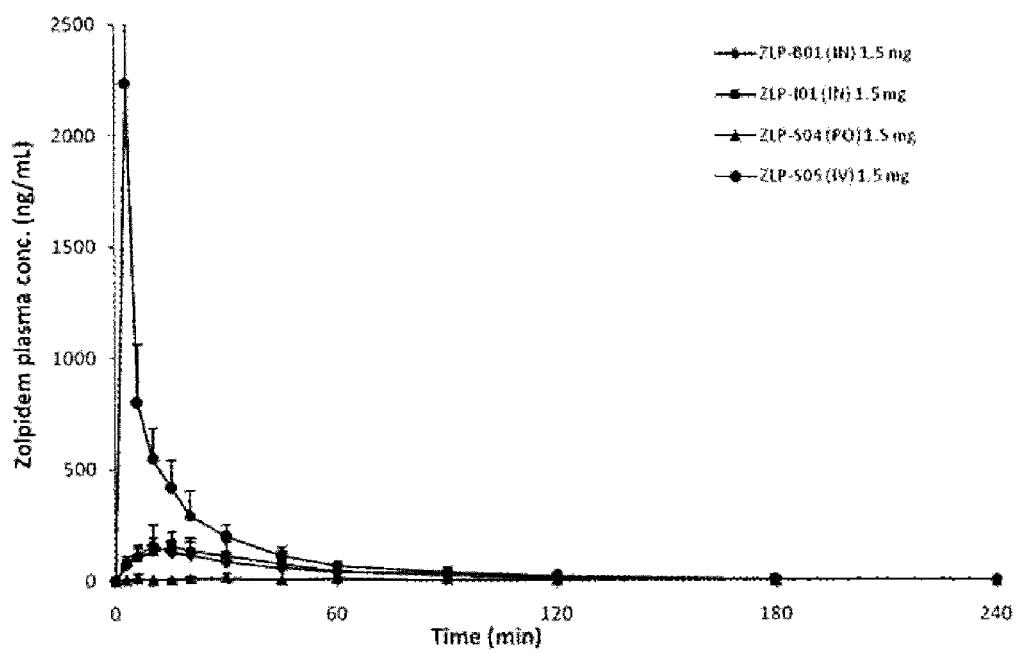
FIG. 3 schematically depicts the mean zolpidem plasma concentration vs. time profiles after intranasal (IN), peroral (PO), and intravenous (IV) administration of various zolpidem formulations in rabbits. In the experiment shown, the zolpidem dose was 1.5 mg per rabbit for all formulations. Data are shown as Mean±SD, n=7-8. Details are described in Example 10.

Profiles of plasma concentration versus time are shown in FIG. 3. They indicate that intranasal administration of the two intranasal formulations (Formulation II and Formulation IV) result in significantly higher plasma zolpidem concentration ($C_{max}$) than the oral administration of zolpidem solution, with earlier onset ($T_{max}$). The pharmacokinetic parameters are summarized in Table 9.

TABLE 9

Pharmacokinetic parameters on intranasal, oral, and intravenous administration of various zolpidem formulations in rabbits (n = 7-8)

| PK Parameters | Intranasal (n = 8) | | Oral (n = 7) | Intravenous (n = 8) |
|---|---|---|---|---|
| | ZLP-B01 | ZLP-I01 | ZLP-S04 | ZLP-S05 |
| $C_{max}$ (ng/ml) | 165 ± 87 | 155 ± 63 | 15 ± 19 | 2237 ± 1811 |
| $T_{max}$ (min) | 13 ± 4 | 15 ± 5 | 30 ± 21 | 3 ± 0 |
| $AUC_{0-4h}$ (ng·min/ml) | 7583 ± 3099 | 8236 ± 3375 | 908 ± 778 | 24616 ± 7117 |
| $AUC_{0-\infty}$ (ng·min/ml) | 7736 ± 3039 | 8335 ± 3362 | 952 ± 804 | 24700 ± 7125 |
| $T_{1/2}$ (min) | 40.6 ± 6.3 | 37.9 ± 7.4 | 33.4 ± 8.4 | 30.5 ± 3.7 |
| F (%) | 32.7 ± 14.9 | 33.8 ± 8.6 | 4.1 ± 3.8 | — |

Example 11

Pharmacokinetic Study in Beagle Dogs

This study was aimed at evaluating the pharmacokinetic parameters of zolpidem intranasal spray (ZLP-B01) as compared to marketed oral tablet in beagle dogs.

Eight beagle dogs (4 male and 4 female) participated in the study. Dogs were given the test articles (ZLP-B01) after an overnight fast before oral dosing but not for intranasal administration. Water was given ad libitum throughout the study. Food was provided 4 hours post-dose. Blood samples were collected at pre-dose (0 min) and at 3, 6, 9, 12, 15, 20, 30, 45 minutes; and at 1, 1.5, 2, 3, 4, 6, 8, 24 hours post-dose. After plasma-separation process, the samples were analyzed by a validated LC-MS/MS method.

Figure 4A:
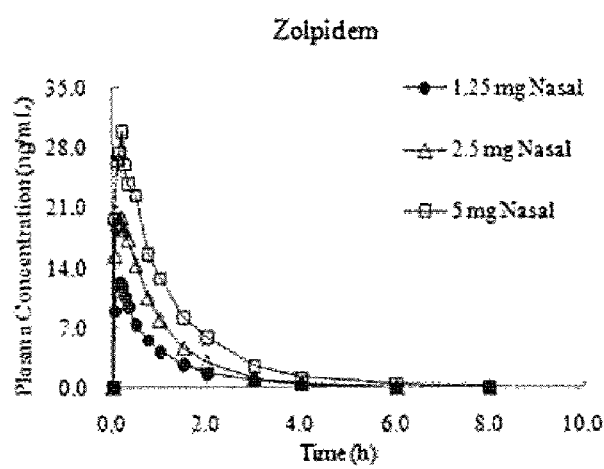
FIG. 4A schematically depicts mean zolpidem plasma concentration-time profiles after intranasal administration to 8 beagle dogs.
Figure 4B:
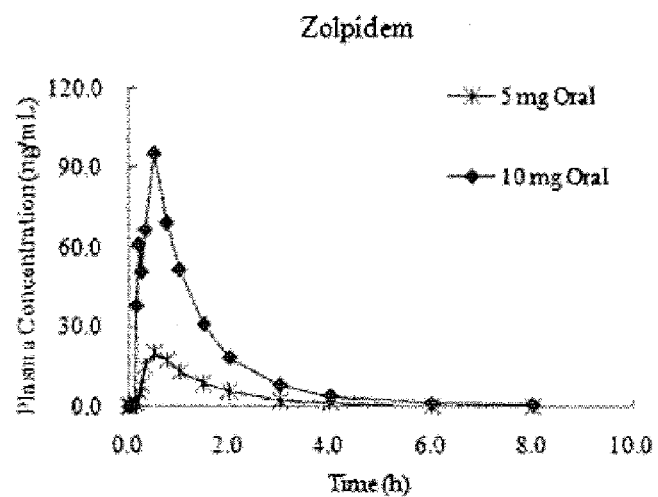
FIG. 4B schematically depicts mean zolpidem plasma concentration-time profiles after oral administration to 8 beagle dogs. Details are described in Example 11.

All dogs were exposed to ZLP-B01 and all plasma samples were analyzed for zolpidem and its four major metabolites (TC015002, TC015001, Z650015 and Z650010). Profiles of plasma concentration versus time are shown in FIG. 4. In this study the intranasal bioavailability of zolpidem was investigated based on the systemic exposures of zolpidem by intranasal administration at doses of 1.25, 2.5 and 5 mg/dog as compared to that by oral administration at 5 and 10 mg/dog. The pharmacokinetic parameters are summarized in Table 10.

TABLE 10

Mean pharmacokinetic parameters and relative bioavailability of zolpidem in beagle dogs

| | Drug Zolpidem Route | | | | |
|---|---|---|---|---|---|
| | Intranasal Administration | | | Oral Administration | |
| | Dosage (mg/dog) | | | | |
| PK Parameter | 1.25 Mean ± SD | 2.5 Mean ± SD | 5 Mean ± SD | 5 Mean ± SD | 10 Mean ± SD |
| $C_{max}$ (ng/mL) | 13.03 ± 6.36 | 21.99 ± 13.08 | 33.34 ± 21.81 | 25.54 ± 18.90 | 128.03 ± 59.74 |
| $T_{max}$ (hour) | 0.14 ± 0.03 | 0.14 ± 0.07 | 0.21 ± 0.13 | 0.69 ± 0.56 | 0.43 ± 0.19 |
| $t_{1/2}$ (hour) | 0.95 ± 0.18 | 0.73 ± 0.23 | 1.14 ± 0.19 | 0.96 ± 0.17 | 0.99 ± 0.21 |
| MRT (hour) | 1.13 ± 0.18 | 1.24 ± 0.83 | 1.50 ± 0.33 | 1.67 ± 0.46 | 1.33 ± 0.30 |
| CL/F (L/hour) | 110 ± 41 | 144 ± 76 | 181 ± 137 | 204 ± 96 | 110 ± 69 |

TABLE 10-continued

Mean pharmacokinetic parameters and relative bioavailability of zolpidem in beagle dogs

| | Drug Zolpidem | | | | |
|---|---|---|---|---|---|
| | Route | | | | |
| | Intranasal Administration | | | Oral Administration | |
| | Dosage (mg/dog) | | | | |
| PK Parameter | 1.25 Mean ± SD | 2.5 Mean ± SD | 5 Mean ± SD | 5 Mean ± SD | 10 Mean ± SD |
| Vz/F (L/hour) | 146 ± 44 | 148 ± 78 | 282 ± 190 | 266 ± 94 | 148 ± 84 |
| $AUC_{0\text{-}last}$ (μg/L * hour) | 12.81 ± 5.24 | 22.20 ± 12.18 | 37.95 ± 18.47 | 30.62 ± 16.85 | 120.20 ± 64.36 |
| $AUC_{0\text{-}\infty}$ (μg/L * hour) | 12.90 ± 5.20 | 22.42 ± 12.12 | 38.05 ± 18.52 | 30.73 ± 16.93 | 120.57 ± 64.58 |
| Rel $F_{(5\ mg\ oral)}$ (%) | 167 | 145 | 124 | — | — |

At a dose of 5 mg/dog, the mean $T_{max}$ of zolpidem was 0.21 hours (ranged 0.050-0.25) by intranasal administration as compared to 0.69 hours (ranged 0.33-2.00) by oral administration. This finding indicated that the absorption of zolpidem by the intranasal route was faster than that by oral dosing. The mean $C_{max}$ of 33.34 ng/mL and $AUC_{0\text{-}last}$ of 37.95 μg/L*hour by intranasal administration were slightly higher than the mean $C_{max}$ of 25.54 ng/mL and $AUC_{0\text{-}last}$ of 30.62 μg/L*hour by oral administration. The terminal half lives were similar for both dose administrations.

Three major metabolites, TC015002, TC015001 and Z650015 were found in all dose levels. A fourth metabolite, Z650010, was not detected after intranasal dosing of all 3 formulations, and only detected in certain dogs (below 0.5 ng/ml) after oral dosing of at 5 and 10 mg Stillnox® tablets. Therefore no PK parameters were reported for Z650010. The amounts of metabolites TC015001 and Z650015 were at least twice as much in the plasma after oral dosing as compared to intranasal administration. This is an example of how determining the concentration of one or more zolpidemmetabolites can be used to determine the efficacy of the zolpidem composition administered to a subject.

Figure 5:
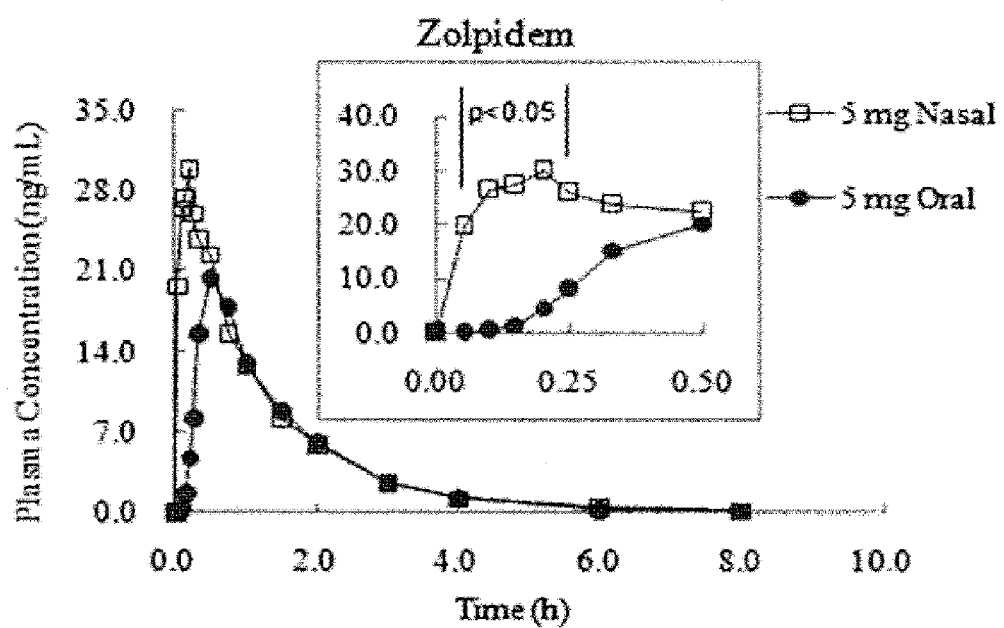
FIG. 5 schematically depicts mean zolpidem plasma concentration-time profiles between intranasal administration of ZLP-B01(III) (5 mg) and oral administration of Stilnox® Tablet (5 mg) in dogs. Details are described in Example 11.

Results indicated that the absorption of zolpidem by intranasal administration was faster than that by oral administration, with significant earlier and higher drug plasma concentration (FIG. 5).

Example 12

Nasal Ciliotoxicity Evaluation in Toads

The nasal ciliotoxicity of zolpidem tartrate, solubilizing agents and several nasal solution formulations were investigated using an in-situ toad palate model. Briefly, 0.2 ml test formulations were administered on a toad palate. 4 h later, the test drug fluid (ZLP-B01) was washed away with saline, and one piece of about 3×3 mm was dissected out from the palate. The mucocilia was examined with a light microscope at enlargements of 400× (n=3~6). Saline and a typical nasal mucociliary toxic agent—sodium deoxycholatee—were used as a negative and positive control, respectively. Study protocol was illustrated in Table 11, and the degree of ciliotoxicity caused by the test formulations was coarse classified as follows: "no effect": cilia on the mucosa was intact, dense and beating actively; "mild": less than 25% ciliostasis; "moderate": cilia was disarranged or only partial cilia left; "severe": all cilia lost and apical cell border was severe deformed.

Optical microscopic observation of toad palate showed that there were a great number of cilia with a fast rate of beating on the edge of mucosa treated with zolpidem tartrate solution (ZLP-B01) and zolpidem tartrate ion-sensitive in-situ gel (ZLP-I01) for 4 h, suggesting the ciliotoxicity of both formulations is mild. While the ciliotoxicity of nasal solution is somewhat greater than that of in-situ gel, with more static cilia visualized. The results indicate that zolpidem tartrate is a safe drug which is suitable for nasal administration. More details are shown in Table 11.

TABLE 11

| Samples | Optical microscopic observation | Ciliotoxicity |
|---|---|---|
| Saline (negative control) | cilia on the mucosa were intact, dense and beat actively | no effect |
| 1% sodium deoxycholate (positive control) | no cilia on the mucosa was observed | severe |
| Blank gel formulation | A great number of cilia; the majority of cilia beat actively and less than 10% cilia were stasis | mild |
| Blank solution formulation | Similar phenomena with that of saline | no effect |
| Zolpidem in-situ gel (ZLP-I01) | A great number of cilia; the majority of cilia beat actively, and less than 25% cilia were stasis or beat slowly | mild |
| Zolpidem nasal solution (ZLP-B01) | A great number of cilia; partial cilia beat fast and partial cilia beat slowly or were immovable | Mild to moderate |

Example 13

Nasal Ciliotoxicity Evaluation in Rats

Sprague-Dawley (SD) rats (200-250 g) were randomly divided into 4 groups (n=3/group). Group 1-2 rats were dosed intranasally with saline and a typical nasal mucociliary toxic agent—sodium deoxycholate—as negative and positive controls, respectively. Group 3 rats were dosed intranasally with 0.875 mg zolpidem tartrate in solution formulation (ZLP-B01). Group 4 rats were dosed intranasally with 0.875 mg zolpidem tartrate in ion-sensitive in-situ gel formulation (ZLP-I01).

For intranasal dosing, 50 μL of dosing solution (saline, sodium deoxycholate solution, ZLP-B01, ZLP-I01) were administered once daily for 7 days to the right lateral nostril of each rat via a polyethylene 10 tube attached to a microliter syringe. Twenty-four hours after the last dose, the rats were sacrificed by injecting an overdose anesthetics and the nasal septum mucosa were peeled off carefully and washed with saline.

For routine histopathological preparations, tissue samples were fixed with 10% formalin, dehydrated in graded ethanol (50, 70, 80, 90, 95 and 100%), vitrificated by dimethylbenzene and then embedded in paraffin. Five-micrometer thick tissue sections were prepared and stained with haematoxylin-eosin (H&E). Tissues were examined using a light microscope (Axiovert 200MAT, Carl Zeiss, Germany).

For scanning electron microscope inspection (SEM), the tissue samples were fixed with 2.5% glutaraldehyde and 1% osmic acid. After dehydration twice sequentially in a graded series of ethanol, the tissues were treated with n-amyl acetate, dried at the critical point of carbon dioxide, and coated with gold by an ion coater. The mucocilia were examined under a scanning electron microscope (JSM-T300, Japan).

The histopathological results show that after intranasal administration of zolpidem tartrate solution (ZLP-B01) and ion-sensitive in-situ gel formulation (ZLP-I01), no significant change in the cell morphology of the nasal mucosa was observed. Occasional loss of the epithelium cells were seen in some areas in the gel group, and slight disruption of some parts of the epithelium and local hyperemia could be found in some regions in the solution group, which indicated that these two formulations had stimulus to the nasal mucosa to some extent. Taking the whole phenomenon into consideration, the cell morphology and differentiation of them were similar to those of the negative control group, which demonstrated that the compositions used had good safety for intranasal administration.

The SEM results indicate that after intranasal administration of zolpidem tartrate solution formulation (ZLP-B01) and zolpidem tartrate ion-sensitive in-situ gel formulation (ZLP-I01), no significant change in the morphology and integrity of the cilia was observed, while small areas of the mild lesion could be seen, which indicated that these two formulations might have slightly irritation to the nasal mucosa. The cilia of the gel group sometimes appeared atrophic, looking clumped together. This could be that gellan gum, an ion-sensitive polymer, changes conformation producing adhesive gel upon contact with the nasal mucosa, which glued together the cilia, giving rise to this appearance of deformity. In conclusion, the SEM results confirmed these two formulations had mild nasal ciliotoxicity and supported its safety in intranasal administration applications.

Example 14

7-Day Dose Range Finding Study of ZNS Intranasally Administered in SD Rats

Sprague-Dawley rats were assigned into six (6) dose groups: one control group, two ZNS oral groups (30, 60 mg/kg), and three ZNS intranasal dose groups (0.208 mg/rat, 0.416 mg/rat, 0.832 mg/rat). Each group comprised 3 males and 3 females. All animals were dosed once daily for 7 consecutive days. General state of animals was recorded daily; food consumption and body weights were measured after dosing; urine samples were collected on Day 7; hematology, clinical chemistry and gross pathology observations were performed at necropsies; the organs were also weighed. Blood samples for TK analysis were collected at the predesigned time points on Day 1 and Day 7, respectively. To further compare the systemic exposure between oral and intranasal routes, one additional oral group was designed at the dose of 8 mg/kg ZLP-B01 and volume of 1 mL/kg. Animals in this group were also bled for TK analysis.

After oral or intranasal administration of ZNS during the 7-day study period, animals in oral groups (30, 60 mg/kg) and high intranasal dose group (0.832 mg/rat) exhibited transient myasthenia of limbs, prostration, hypoactivity post-dose. No abnormality was found in body weights, food consumption, hematology, clinical chemistry, urinalysis, organ weights/ratios, and gross pathology observations. The no observed adverse effect levels (NOAEL) were established to be 60 mg/kg for oral administration and 0.832 mg/rat for intranasal administration, respectively.

After intranasal administration of ZOL at the dose range of 0.208~0.832 mg/rat, the drug exposure level (AUC) is linear for both sexes. No drug accumulation was found in all study groups. The female rats have higher exposure level than the male rats in all oral groups. The time to peak plasma concentration ($T_{max}$) of intranasal groups was shorter than that of oral group for both sexes. In male rats, similar exposure levels were found after a single intranasal dose of 0.832 mg/rat and a single oral dose of 8 mg/kg; in female rats, higher exposure level was shown after a single oral dose of 8 mg/kg, as compared to a single intranasal dose of 0.832 mg/rat).

Example 15

30-Day Toxicity and Toxicokinetics Study of Zolpidem Tartrate Nasal Spray (ZOL) Intranasally Administered to Sprague-Dawley Rats In this study, 190 rats (95 animals/sex) were assigned into five (5) dose groups: three ZOL intranasal groups (0.207/rat, 0.413 mg/rat and 0.826 mg/rat) groups, a intranasal control group, a ZOL oral group (4 mg/kg for female, 8 mg/kg for male). For intranasal ZOL groups and control group, each rat received 40 μL ZOL (5.2, 10.4 and 20.8 mg/mL) or vehicle solution by nasal dripping once daily; for oral group, each rat received ZOL solution (1 mL/kg) via oral gavage once daily. Rats were intranasally and orally dosed with ZOL or vehicle solution for consecutive 30 days, followed by a 14-day recovery period. The clinical signs observation was conducted daily, body weight and food consumption was recorded after dosing, urine samples were collected on the day before necropsy in treatment and recovery periods, the ophthalmic examination was performed once pre-necropsy. The examinations of hematology, clinical chemistry, bone marrow slides and gross pathology observations were performed at necropsies and the organ weights were also recorded. Blood samples for TK analysis were collected at the pre-designed time points on Day 1 and Day 30, respectively.

Clinical Observations:

All males and part of females in ZOL oral group and ZOL intranasal high dose group (0.832 mg/rat/day) exhibited transient drug-related pharmacological effects after dosing, such as hypoactivity, which was sporadic in ZOL intranasal intermediate dose group (0.416 mg/rat/day). After waking up, no abnormality was observed in respiration, nasal mucous membrane, nostril and surrounding hair, movement, and appetite of these animals.

Body Weight and Food Consumption:

No abnormal changes were found in the body weight and food consumption during the treatment and recovery periods.

Hematology:

No abnormalities were found in RBC, HGB, RET %, WBC, PLT and PT at the end of the treatment and recovery periods.

Clinical Chemistry:

No drug-related abnormalities were found in ALP, ALT, AST, TP, ALB, GLU, TBIL, CHOL, TG, CK, Urea, Crea, AMY-P, LIP, K+, Na−, P, and Cl− at the end of the treatment and recovery periods.

Urinalysis:

At the end of treatment and recovery periods, no abnormalities were found in urine routine, urine sediment or urinary volume.

Organ Weights and Ratios:

At the end of treatment and recovery periods, no abnormalities were found in the organ weight and ratios of brain, heart, liver, spleen, lung, kidney, adrenal gland.

Bone Marrow Slides:

At the end of treatment and recovery periods, no abnormalities were found in granulocytic series, erythrocytic series, lymphocyte cell, mononuclear cell, megakaryocyte count.

Gross Pathology Observations:

At the end of treatment and recovery periods, no abnormalities were noted in nasal mucous membrane, pars laryngea pharyngis, eyeball, heart, liver, spleen, kidney, lung, adrenal gland, testis, ovary, uterus, epididymis, thymus, etc.

Histopathology:

Minimal to slight monocytes infiltration of the nasal cavity was found in animals exposed to ZOL, the frequency and intensity were dose-related. No monocytes infiltration was found at the end of recovery period. No abnormal histopathological findings were observed in other major organs and tissues such as heart, liver, lung, spleen, thymus, adrenal gland, ovary, uterus, testis, epididymis, nasal bone, pars laryngea pharynges.

Ophthalmic Examinations:

At the end of treatment and recovery periods, no abnormalities were found on dioptric media, discus opticus, macula lutea, macular arch, arterina retina, vein, retina or optic disc.

TK Analysis:

The time to peak plasma concentration ($T_{max}$) in ZOL intranasal groups was earlier than that in oral group. Drug exposure levels (AUC) were linear for both genders. For intranasal low and intermediate groups, higher exposure levels were achieved in females as compared to the males, for intranasal high dose group, comparable exposure levels were found between males and females. Comparable exposure levels were also achieved between intranasal high dose group and oral dose group.

The $AUC_{Day30}/AUC_{Day1}$ ratio was less than or near 1 for both genders in ZOL groups, suggesting the absence of drug accumulation after repeated dosing for 30 consecutive days.

The No-Observed-Adverse-Effect Level (NOAEL) was found to be to be 0.826 mg/rat for intranasal administration of ZOL.

What is claimed is:

1. A pharmaceutical composition, comprising:
 (i) a compound having Formula I:

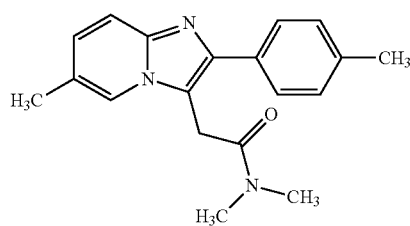

Formula I or single stereoisomer, mixtures of stereoisomers, pharmaceutically acceptable salts or prodrugs thereof;

(ii) HP-β-cyclodextrin; and
 (iii) at least one aqueous vehicle polymer capable of changing in a nasal fluid a rheological behavior in relation to pH change, in relation to temperature change, or in the presence of ions.

2. The pharmaceutical composition of claim 1, further comprising
 (iv) an aqueous solvent vehicle suitable for intranasal spray using a spray device.

3. The pharmaceutical composition of claim 1, wherein (i) is at a concentration between about 5 mg/ml and about 100 mg/ml.

4. The pharmaceutical composition of claim 1, wherein HP-β-cyclodextrin is at a concentration of about 50 mg/ml to about 600 mg/ml.

5. The pharmaceutical composition of claim 2, which has a pH from about 3.0 to about 9.

6. The pharmaceutical composition of claim 1, further comprising:
 (v) a bioadhesive polymeric material.

7. The pharmaceutical composition of claim 6, wherein the bioadhesive polymer material is carboxymethylcellulose sodium.

8. The pharmaceutical composition of claim 7, wherein the carboxymethylcellulose sodium is at a concentration of about 1 mg/ml to about 50 mg/ml.

9. The pharmaceutical composition of claim 6, wherein the bioadhesive polymer is hydroxypropyl methylcellulose.

10. The pharmaceutical composition of claim 9, wherein the hydroxypropyl methylcellulose is at a concentration of about 1 mg/ml to about 50 mg/ml.

11. The pharmaceutical composition of claim 6, wherein the bioadhesive polymer is sodium alginate.

12. The pharmaceutical composition of claim 11, wherein the sodium alginate is at a concentration of about 1 mg/ml to about 50 mg/ml.

13. The pharmaceutical composition of claim 1, further comprising:
 (v) a polymer capable of substantially lowering vehicle viscosity without any ion and substantially increasing the viscosity after intranasal administration of the pharmaceutical composition triggered by the ions in nasal fluid.

14. The pharmaceutical composition of claim 13, wherein the polymer is selected from the group consisting of gellan gum and pectin.

15. The pharmaceutical composition of claim 14, wherein the gellan gum is at a concentration of about 1 mg/ml to 20 mg/ml and the pectin is at a concentration of about 0.1 mg/ml to about 10 mg/mi.

16. The pharmaceutical composition of claim 2, further comprising:
 (v) a polymer capable of substantially lowering vehicle viscosity at room temperature and substantially increasing the viscosity after intranasal administration of the pharmaceutical composition triggered by a change in body temperature.

17. The pharmaceutical composition of claim 16, wherein the polymer is selected from the group consisting of Poloxamer407® and Poloxamer188®.

18. The pharmaceutical composition of claim 17, wherein the Poloxamer407® is at a concentration of about 50 mg/ml to about 300 mg/ml and the Poloxamer188® is at a concentration of about 5 mg/ml to 50 mg/ml.

19. A method for treating an insomnia related disorder in a subject, the method comprising the step of:

administering to a subject having insomnia or an insomnia-related disorder or being at risk of developing insomnia or an insomnia-related disorder a pharmaceutically effective amount of a pharmaceutical composition claim 1.

20. An intranasal spray application kit comprising:

a pharmaceutical composition of claim 1; and (ii) an actuation mechanism for providing a spray volume of about 0.05 to about 0.15 ml per actuation.

* * * * *